United States Patent
Fleming et al.

(10) Patent No.: US 10,058,306 B2
(45) Date of Patent: Aug. 28, 2018

(54) METHOD FOR OBTAINING FETAL CELLS AND FETAL CELLULAR COMPONENTS

(71) Applicant: QuantRx Biomedical Corporation, Tualatin, OR (US)

(72) Inventors: William H. Fleming, Canby, OR (US); Shalom Z. Hirschman, Bronx, NY (US)

(73) Assignee: Preprogen, LLC, Monroe, NY (US)

( * ) Notice: Subject to any disclaimer, the term of this patent is extended or adjusted under 35 U.S.C. 154(b) by 0 days.

(21) Appl. No.: 14/410,508

(22) PCT Filed: Jun. 24, 2013

(86) PCT No.: PCT/US2013/047383
§ 371 (c)(1),
(2) Date: Dec. 22, 2014

(87) PCT Pub. No.: WO2013/192620
PCT Pub. Date: Dec. 27, 2013

(65) Prior Publication Data
US 2015/0342577 A1   Dec. 3, 2015

Related U.S. Application Data

(60) Provisional application No. 61/663,456, filed on Jun. 22, 2012.

(51) Int. Cl.
| | |
|---|---|
| *A61B 10/00* | (2006.01) |
| *C12N 5/0735* | (2010.01) |
| *A61F 13/84* | (2006.01) |
| *A61B 10/02* | (2006.01) |
| *C12Q 1/6879* | (2018.01) |

(52) U.S. Cl.
CPC .......... *A61B 10/0048* (2013.01); *A61B 10/02* (2013.01); *A61B 10/0291* (2013.01); *A61F 13/84* (2013.01); *C12N 5/0606* (2013.01); *C12Q 1/6879* (2013.01); *A61B 2010/0074* (2013.01); *A61F 2013/8473* (2013.01); *G01N 2800/36* (2013.01)

(58) Field of Classification Search
CPC ............. A61F 2013/8473; A61F 13/84; G01N 2800/36; A61B 10/0048; A61B 10/02; A61B 10/0291; A61B 2010/0074; C12N 5/0606; C12Q 1/6879
See application file for complete search history.

(56) References Cited

U.S. PATENT DOCUMENTS

| | | |
|---|---|---|
| 2,905,169 A | 9/1959 | Nieburgs |
| 3,983,873 A | 10/1976 | Hirschman |
| 4,095,542 A | 6/1978 | Hirschman |
| 4,142,476 A | 3/1979 | Hirschman |
| 4,675,286 A * | 6/1987 | Calenoff ................ A61B 10/02 435/30 |
| 4,995,150 A | 2/1991 | Gerstenberger et al. |
| 5,124,252 A | 6/1992 | Guerrant et al. |
| 5,190,881 A | 3/1993 | McKibbin |
| 5,459,034 A | 10/1995 | Tabaqchali et al. |
| 5,538,851 A | 7/1996 | Fach et al. |
| 5,575,047 A | 11/1996 | Gerstenberger et al. |
| 5,625,105 A | 4/1997 | Lin et al. |
| 5,661,010 A | 8/1997 | De Lourdes Munoz Moreno |
| 5,725,841 A | 3/1998 | Duan et al. |
| 5,727,481 A | 3/1998 | Voorhees et al. |
| 5,965,375 A | 10/1999 | Valkirs |
| 5,968,026 A | 10/1999 | Osborn, III et al. |
| 6,007,498 A | 12/1999 | Buck et al. |
| 6,155,990 A | 12/2000 | Fournier |
| 6,174,293 B1 | 1/2001 | Buck et al. |
| 6,183,455 B1 | 2/2001 | Gerstenberger et al. |
| 6,300,071 B1 | 10/2001 | Vuylsteke et al. |
| 6,569,684 B2 | 5/2003 | Chai et al. |
| 6,743,212 B1 | 6/2004 | Cole et al. |
| 6,811,549 B2 | 11/2004 | Fleming |
| 7,035,739 B2 | 4/2006 | Schadt et al. |
| 7,037,650 B2 | 5/2006 | Gonzalgo et al. |
| 7,091,395 B2 | 8/2006 | Pasquini et al. |

(Continued)

FOREIGN PATENT DOCUMENTS

| | | |
|---|---|---|
| WO | WO1990006509 | 6/1990 |
| WO | WO1991007660 | 5/1991 |

(Continued)

OTHER PUBLICATIONS

American Pregnancy Association, "Amniocentesis," available at: http://americanpregnancy.org/prenatal-testing/amniocentesis/, last accessed Dec. 19, 2014.
Bischoff, et al. "Cell-free fetal DNA and intact fetal cells in maternal blood circulation: implications for first and second trimester non-invasive prenatal diagnosis." *Human reproduction update* 8 (2002): 493-500.
El-Messidi, et al. "Diagnosis of premature rupture of membranes: inspiration from the past and insights for the future." *Journal of obstetrics and gynaecology Canada* 32 (2010): 561-569.

(Continued)

*Primary Examiner* — Andrea S Grossman
(74) *Attorney, Agent, or Firm* — Klarquist Sparkman, LLP

(57) ABSTRACT

Methods are disclosed for non-invasively obtaining fetal cells from a pregnant female. The methods include placing an absorbent medium in an interlabial or intravaginal space or adjacent to the perineum at the vaginal opening of the pregnant female, and collecting vaginal fluid comprising cells in the absorbent medium while the absorbent medium is interlabial or intravaginal space or adjacent to the perineum at the vaginal opening. The absorbent medium is removed and cells are isolated from the absorbent medium to obtain the fetal cells. The fetal cells can be, for example, somatic cells, embroyic stem cells, fetal stem cells or trophoblast cells.

14 Claims, 11 Drawing Sheets

(56) References Cited

U.S. PATENT DOCUMENTS

| | | | |
|---|---|---|---|
| 7,144,701 B2 | 12/2006 | Huang | |
| 7,341,737 B2 | 3/2008 | Gehling et al. | |
| 7,713,253 B2 | 5/2010 | Osborn, III et al. | |
| 8,021,876 B2 | 9/2011 | Atala et al. | |
| 2003/0013123 A1 | 1/2003 | Mahoney et al. | |
| 2005/0042595 A1* | 2/2005 | Haas | C12N 5/0605 435/2 |
| 2005/0124003 A1 | 6/2005 | Atala et al. | |
| 2008/0113358 A1* | 5/2008 | Kapur | G01N 33/689 435/6.12 |
| 2009/0081689 A1* | 3/2009 | Yamanishi | G01N 33/56966 435/6.11 |
| 2010/0030189 A1 | 2/2010 | Fleming | |
| 2010/0311190 A1 | 12/2010 | Fuks et al. | |
| 2011/0027795 A1* | 2/2011 | Mantzaris | C12N 5/0603 435/6.12 |
| 2011/0166432 A1 | 7/2011 | Fleming | |
| 2012/0108460 A1 | 5/2012 | Quake et al. | |

FOREIGN PATENT DOCUMENTS

| | | |
|---|---|---|
| WO | WO1995026417 | 10/1995 |
| WO | WO 1997/43955 | 11/1997 |
| WO | WO1998002528 | 1/1998 |
| WO | WO1998018005 | 4/1998 |
| WO | WO1999002985 | 1/1999 |
| WO | WO2000071987 | 11/2000 |
| WO | WO2003042405 | 5/2003 |
| WO | WO2004076653 | 9/2004 |
| WO | WO2005100401 | 10/2005 |
| WO | WO2007106838 | 9/2007 |
| WO | WO2007112281 | 10/2007 |
| WO | WO 2008/106610 | 9/2008 |
| WO | WO2009039507 | 3/2009 |
| WO | WO2010085841 | 8/2010 |

OTHER PUBLICATIONS

Graves, et al. "Maternal serum triple analyte screening in pregnancy." *American family physician* 65 (2002): 915-920.

Imudia, et al. "Transcervical retrieval of fetal cells in the practice of modern medicine: a review of the current literature and future direction." *Fertility and sterility* 93 (2010): 1725-1730.

Litton, et al. "Noninvasive Prenatal Diagnosis: Past, Present, and Future." *Mount Sinai Journal of Medicine* 76 (2009): 521-528.

Mayo Clinic, "Amniocentesis," available at: http://www.mayoclinic.org/tests-procedures/amniocentesis/basics/definition/prc-20014529, last accessed Dec. 19, 2014.

Merck Manuals, "Prenatal Diagnostic Testing," available at: http://www.merckmanuals.com/home/womens_health_issues/detection_of_genetic_disorders/prenatal_diagnostic_testing.html?qt=&sc=&alt=, last accessed Dec. 22, 2014.

Prusa, Andrea-Romana, et al. "Oct-4-expressing cells in human amniotic fluid: a new source for stem cell research?." *Human reproduction* 18.7 (2003): 1.489-1493.

Purwosunu, et al. "Clinical potential for noninvasive prenatal diagnosis through detection of fetal cells in maternal blood." *Taiwanese Journal of Obstetrics and Gynecology* 45 (2006): 10-20.

Sekizawa, et al. "Recent advances in non-invasive prenatal DNA diagnosis through analysis of maternal blood." *Journal of Obstetrics and Gynaecology Research* 33 (2007): 747-764.

Wong, et al. "Human papillomavirus DNA detection in menstrual blood from patients with cervical intraepithelial neoplasia and condyloma acuminatum." *Journal of clinical microbiology* 48 (2010): 709-713.

Supplementary European Search Report dated by the European Patent Office dated Feb. 9, 2016 for EPC Application No. 13806393.8 (6 pages).

* cited by examiner

Bands in #8 or 9 lanes indicate the presence of Male DNA.

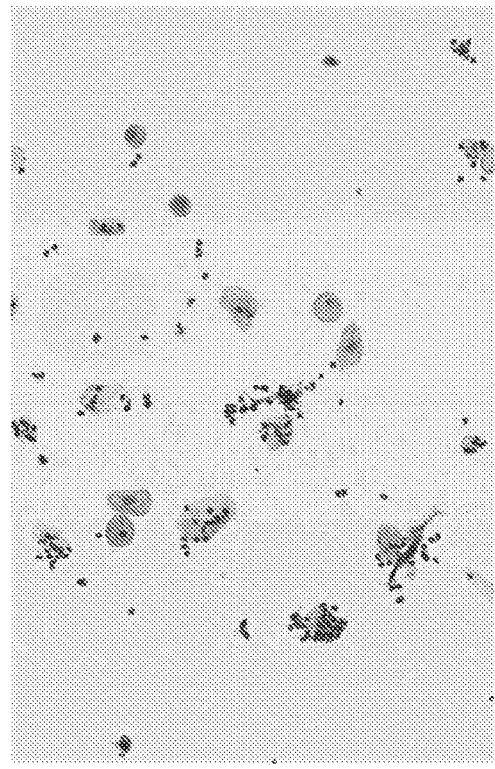
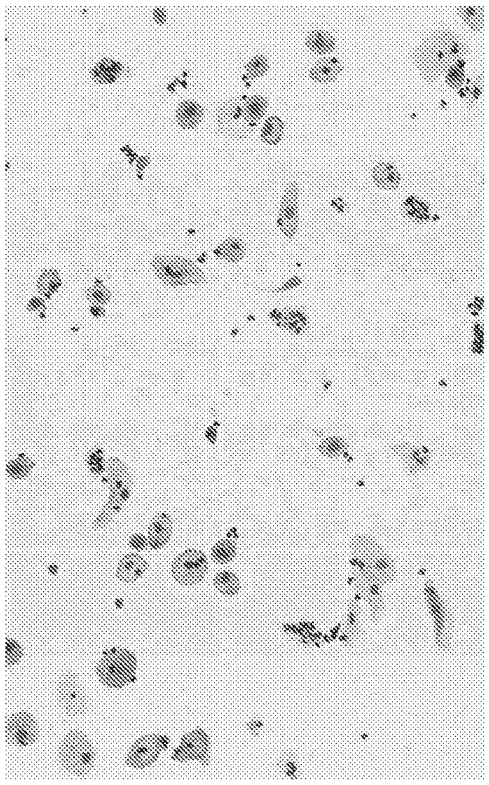
FIG. 4

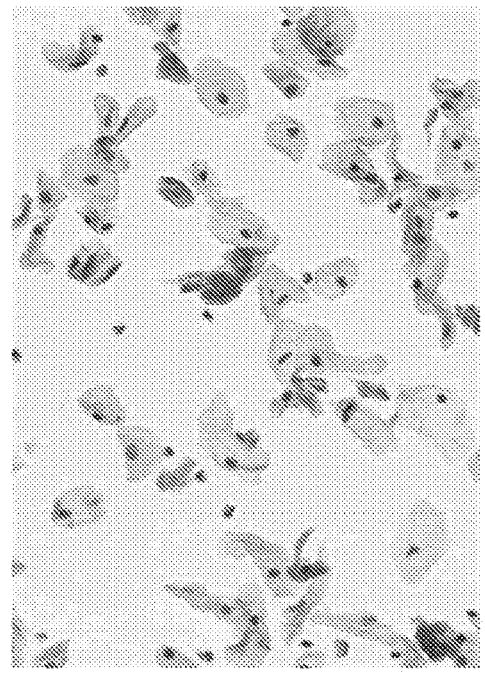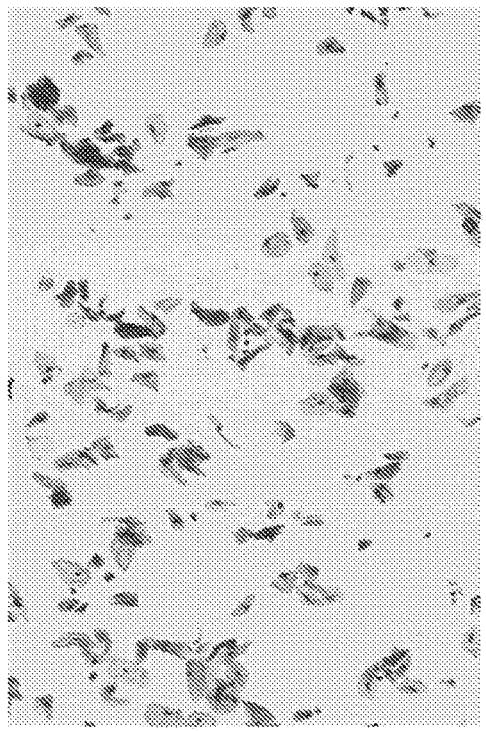
FIG. 5

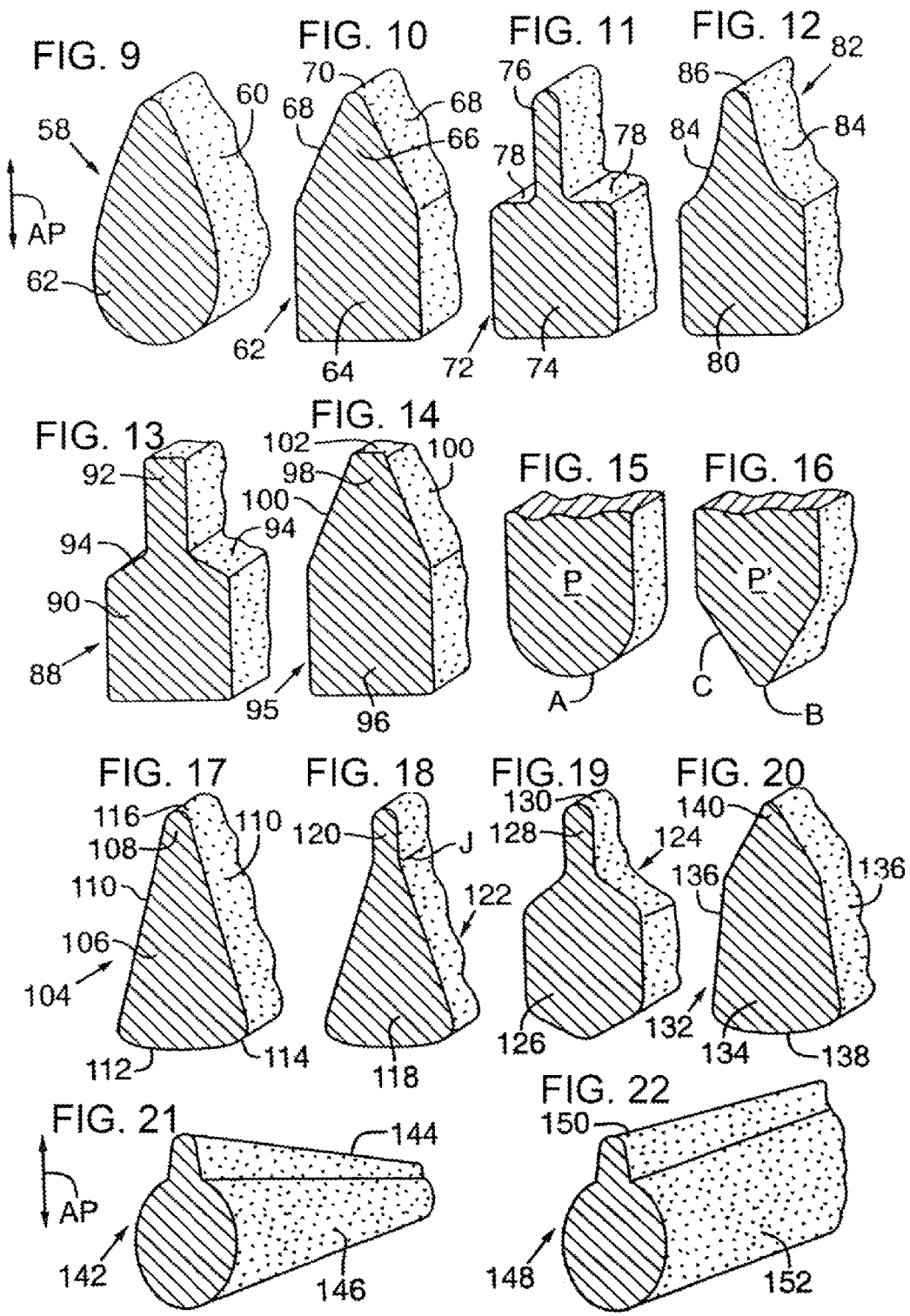

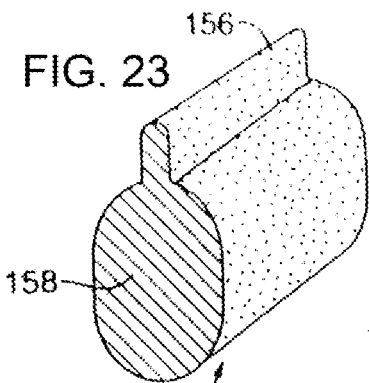
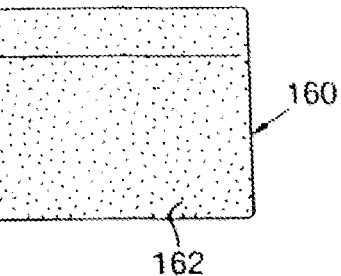
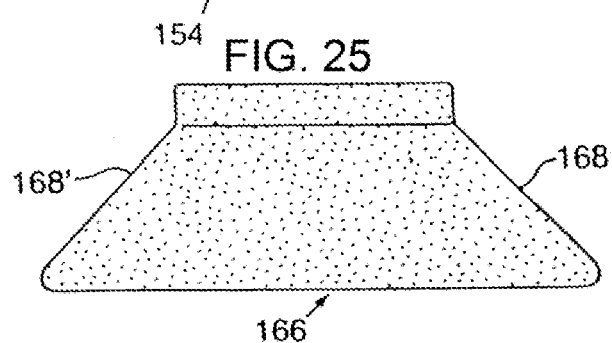
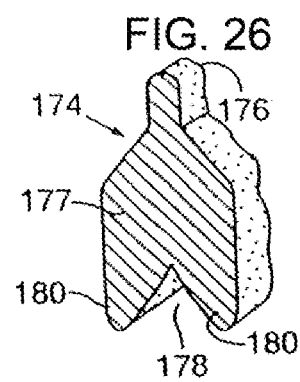
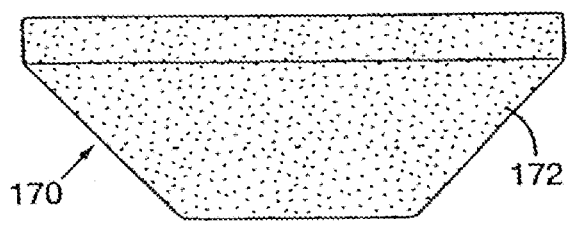
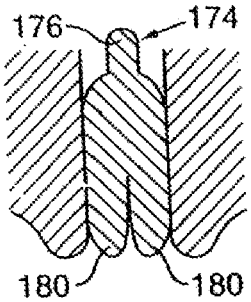
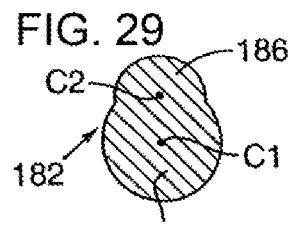
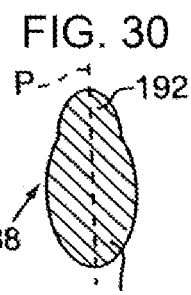
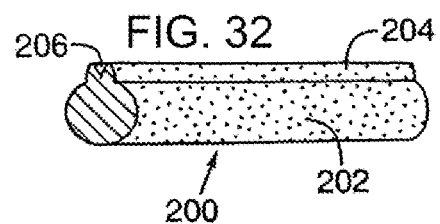
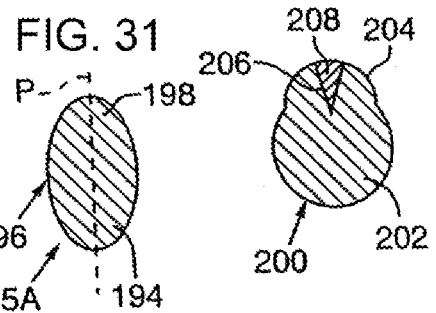

MRI OF PAD AND TAMPON

METHOD FOR OBTAINING FETAL CELLS AND FETAL CELLULAR COMPONENTS

CROSS REFERENCE TO RELATED APPLICATIONS

This is the U.S. National Stage of International Application No. PCT/US2013/047383, filed Jun. 24, 2013, which was published in English under PCT Article 21(2), which in turn claims the benefit of U.S. Provisional Application No. 61/663,456, filed Jun. 22, 2012. The provisional application is herein incorporated by reference in its entirety.

FIELD

This relates to the field of cell purification, specifically to methods for isolating fetal cells from a pregnant woman using non-invasive methods.

BACKGROUND

Amniocentesis is a medical procedure used in prenatal diagnosis of chromosomal abnormalities and fetal infections, in which a small amount of amniotic fluid, which contains fetal tissues, is obtained from the amnion or amniotic sac, and the fetal DNA is examined for genetic abnormalities. This process also can be used for prenatal sex discernment.

Amniocentesis is generally performed between the 15th and 20th week of pregnancy; performing this test earlier may result in fetal injury. The term "early amniocentesis" is sometimes used to describe use of the process between weeks 11 and 13. However, it is not possible to use amniocentisis to obtain DNA or fetal cells from a fetus of less than 11 weeks of gestation. In addition, amniocentesis is invasive.

Amniotic fluid is a source of multipotent mesenchymal, hematopoietic, neural, epithelial, and endothelial stem cells. However, collecting these cells can result in complications. Artificial heart valves, working tracheas, as well as muscle, fat, bone, heart, neural and liver cells have been produced from stem cells isolated from amniotic fluid. Tissues obtained from amniotic cell lines show promise for patients suffering from congenital diseases/malformations of the heart, liver, lungs, kidneys, and cerebral tissue.

However, complications of amniocentesis include preterm labor and delivery, respiratory distress, postural deformities, fetal trauma and alloimmunisation of the mother (rhesus disease). Studies from the 1970s originally estimated the risk of amniocentesis-related miscarriage at around 1 in 200 (0.5%) although other more recent studies estimated the procedure-related pregnancy loss at 0.6-0.86%. Thus, a need remains for other methods that can be used to collect fetal stem cells and that can be used for fetal diagnosis.

SUMMARY

Disclosed are completely new uses of external collection devices, including absorbent interlabial pads, sanitary napkins and tampons. Specifically, it is disclosed herein that these devices can be used for the collection of fetal cells, such as, but not limited to, somatic cells, embryonic stem cells, fetal stem cells or trophoblast cells. Surprisingly, it was determined that fetal cells remain viable in these devices, and can be isolated and propagated following collection. In addition, these devices can be used for the collection of the components of fetal cells, such as DNA, RNA, proteins and lipids.

In some embodiments, methods are provided for obtaining fetal cells and/or fetal cell components from a pregnant female. The methods include placing an absorbent medium in an interlabial or intravaginal space or adjacent to the perineum at the vaginal opening of the pregnant female, and collecting vaginal fluid comprising fetal cells and/or fetal cellular components in the absorbent medium while the absorbent medium is in the interlabial or intravaginal space or adjacent to the perineum at the vaginal opening. The absorbent medium is removed and cells are isolated from the absorbent medium to obtain the fetal cells. The fetal cells can be, for example, somatic cells, embryonic stem cells, fetal stem cells or trophoblast cells.

In additional embodiments, methods are provided for fetal diagnosis. The methods include placing an absorbent medium in an interlabial or intravaginal space or adjacent to a perineum at a vaginal opening of a pregnant female, and collecting vaginal fluid in the absorbent medium. The absorbent medium is removed from the pregnant female, and cells in the absorbent medium are subjected to a fetal diagnostic test. In some embodiments, the method includes isolating at least one fetal cell from the absorbent medium. The genetic material, or genetic material isolated from the at least one fetal cell can be analyzed to determine the presence or absence of a genomic or epigenetic characteristic associated with a biological outcome. In some embodiments, methods are provided for determining the sex of a fetus.

The foregoing and other features and advantages of this disclosure will become more apparent from the following detailed description of several embodiments which proceeds with reference to the accompanying figures.

BRIEF DESCRIPTION OF THE FIGURES

FIG. 4 is a digital image of a cytology evaluation. Upon harvest as a pellet, ½ of each PADKIT® sample was subjected to digital cytometry using standard HOLOGICS® Thin-prep technology and Pap staining performed at a CLIA-certified Cytometry lab. These Thin-prep slides were then analyzed by APERIO® digital Cytometry. Both standard light and digital cytometry confirmed that all samples processed for this study showed ordinary cell morphology, which were indistinguishable relative to routine PAP stained cervical scrapes.

FIG. 5 is a digital image of a second cytology evaluation.

FIG. 9 is a cross sectional fragmentary view of another embodiment of the interlabial pad.

FIGS. 10-14 are views similar to FIG. 4, but showing different embodiments of the pad which have a substantially quadrilateral shape or major portion.

FIGS. 15 and 16 are cross sectional views of the major portion of the pad, showing the major portion to be either arcuate (FIG. 15) or tapered (FIG. 16).

FIG. 17 is a cross sectional view of an interlabial absorbent pad that does not have a major portion and a minor portion, but which has the side surfaces of the pad sloping toward a leading edge of the pad.

FIGS. 18-20 are cross-sectional fragmentary views showing pads, which have major portions that are polygonal in shape.

FIG. 21 is a cross sectional view of an elongated interlabial pad with a major portion and a minor portion, both of which taper symmetrically in a longitudinal direction.

FIG. 22 is a view similar to FIG. 16, but showing the major and minor portions of the pad tapering longitudinally in different directions.

FIG. 23 is a perspective view of an elongated interlabial absorbent pad that has a fixed diameter along the length of the pad.

FIGS. 24-26 are side views of interlabial absorbent pads similar to the pad shown in FIG. 23, but with one or two sloping end edges.

FIG. 27 is a cross sectional view of an interlabial absorbent pad wherein the posterior portion of the pad is formed with a longitudinal groove.

FIG. 28 is a cross sectional view of the interlabial absorbent pad of FIG. 22 disposed between the labia in the interlabial space.

FIG. 29 is a cross sectional view of a unitary, one-piece yet bipartite interlabial absorbent pad in which each portion of the pad has a cross section of a portion of a circle, each circle having different radii of curvature.

FIG. 30 is a cross sectional view of a bipartite pad in which each portion of the pad has a cross section of a partial ellipse. The pads may be either symmetric or asymmetric. In the symmetric embodiment, the major and minor portions may have the shape of partial spheres or ellipsoids.

FIG. 31 is a cross sectional view of an additional embodiment of a one-piece interlabial pad with an elliptical cross section, and no minor and major portions.

FIG. 32 is an end perspective view of an elongated pad with a minor and a major portion that extends along its length, and a groove in the minor portion from which drugs or other agents can be released by compression of the pad in use.

FIG. 33 is an end view of the pad of FIG. 27.

DETAILED DESCRIPTION

Figure 1A:
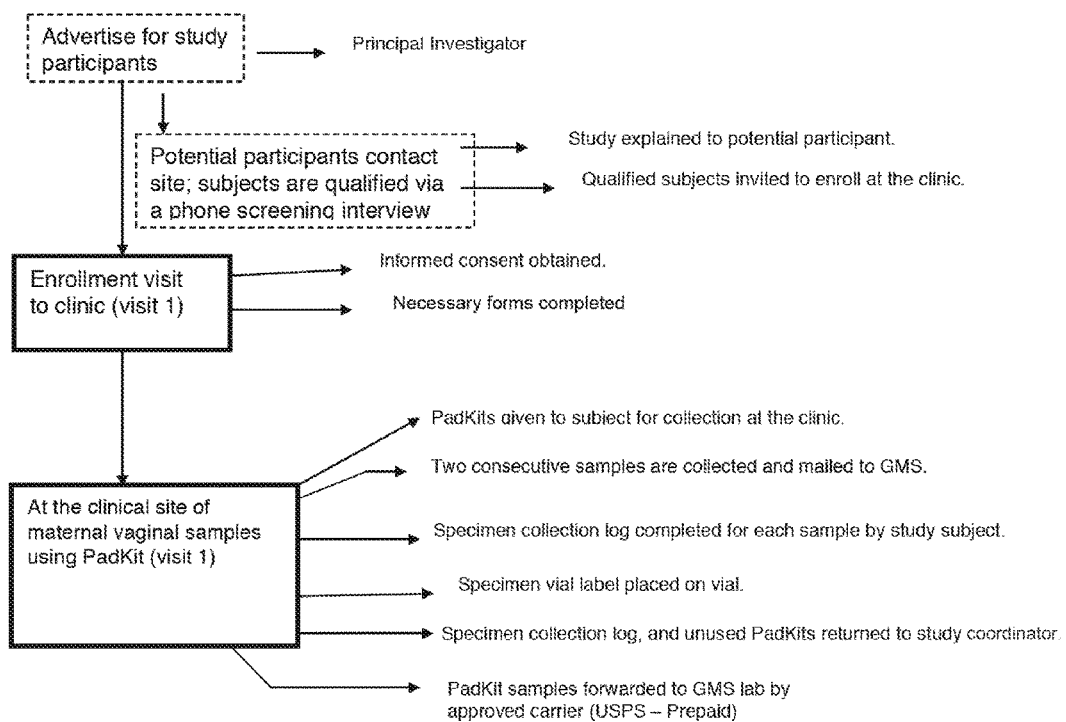
FIGS. 1A and 1B are a set of flow charts illustrating an embodiment of processing of absorbent medium for the collection of fetal cells.

Methods are disclosed for non-invasively obtaining fetal cells from a pregnant female. The methods include placing an absorbent medium in an interlabial or intravaginal space or adjacent to the perineum at the vaginal opening of the pregnant female, and collecting vaginal fluid comprising cells in the absorbent medium while the absorbent medium is interlabial or intravaginal space or adjacent to the perineum at the vaginal opening. The absorbent medium is removed and cells are isolated from the absorbent medium to obtain the fetal cells. The fetal cells can be, for example, somatic cells, embryonic stem cells, fetal stem cells or trophoblast cells.

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Absorbent: A material with sufficient absorbency to absorb and retain exudates discharged from a subject, such as fluids and/or cells. Absorbency is dependent partially on the physical volume of the device. In a specific non-limiting example, a material is absorbent if it absorbs at least 3 ml of 0.9% saline, however an absorbent material may have a capacity of 20 grams or more.

Agent: A substance capable of producing a physical, chemical or biological effect. Examples of agents include drugs (therapeutic agents) and diagnostic reagents (diagnostic agents). Examples of drugs include antimicrobial agents (such as the anti-fungal agent miconazole, anti-viral acyclovir, or anti-biotic metronidazole). Examples of diagnostic agents include monoclonal antibodies (such as monoclonal antibodies that recognize pathologic agents, such as viruses, chemical reagents in which a reaction occurs in the presence of a pathogen of interest, such as a color change), or agents that can be used to diagnose.

Amniotic Sac: The membranes that a fetus develops in amniotes. The inner membrane is the amnion, and the outer membrane is the chorion. On the outer side, the amniotic sac is connected to the allantois and yolk sac, and, through the umbilical cord, to the placenta. An "intact" amniotic sac includes unbroken membranes containing the amniotic fluid. A "ruptured" amniotic sac is one with a broken membrane.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bi-specific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online The sequences of the framework regions of different light or heavy chains are relatively conserved within a species. The framework region of an antibody, that is the combined framework regions of the constituent light and heavy chains, serves to position and align the CDRs in three-dimensional space. The CDRs are primarily responsible for binding to an epitope of an antigen.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies. A "chimeric antibody" has framework residues from one species, such as human, and CDRs (which generally confer antigen binding) from another species, such as a murine antibody. A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Aneuploidy: An abnormal number of chromosomes. Monosomy refers to the presence of only one chromosome, wherein two copies is normal. Monosomy of the X chromosome (45,X) causes Turner's syndrome. Trisomy refers to the presence of three copies (instead of the normal two) of specific chromosomes. Trisomy 21 causes Down's syndrome. Tripsome 10 and Trisomy 31, known as Edwards and Patau Syndrome, respectively, are two autosomal abnormalities. Trisomy X has also been observed in humans (47, XXX).

Germline aneuploidy can be detected through karyotyping, a process in which a sample of cells is fixed and stained to create the typical light and dark chromosomal banding pattern and a picture of the chromosomes is analyzed. Other techniques include Fluorescence In Situ Hybridization (FISH), Quantitative Polymerase Chain Reaction (PCR) of Short Tandem Repeats, Quantitative Fluorescence PCR (QF-PCR), Quantitative Real-time PCR (RT-PCR) dosage analysis, Quantitative Mass Spectrometry of Single Nucleotide Polymorphisms, and Comparative Genomic Hybridization (CGH).

Biodegradable material: A material having greater than or equal to about 70% biodegradation (percentage of theoretical carbon dioxide evolution) after 28 days when measured by a suitable test such as the Sturm test (Method 301B, Organization of Economic Cooperation and Development).

Cellular Components: The biological molecules, such as DNA, RNA, lipids, protein and phospholipids that are contained in a cell. "Fetal cellular components" are biological molecule, such as DNA, RNA, lipids and proteins isolated from fetal cells. Similarly, "maternal cellular components" are biological molecule, such as DNA, RNA, lipids and proteins isolated from cells of a mother of a fetus or baby, such as a pregnant female. "Genetic material" includes both DNA and RNA.

Diagnostic test: Any procedure performed on a biological sample, wherein the procedure can be used to evaluate or monitor a disease or a disorder, or can be used to determine the genotype. Diagnostic tests include tests that analyze the genomic and/or epigenetic characteristics of a fetus by analyzing fetal cells and/or cellular components, such as DNA or proteins. A diagnostic test can be performed in a laboratory, a medical office or in the home environment. A diagnostic test can also be used to determine fetal sex.

DNA methylation: The post synthetic addition of methyl groups to specific sites on DNA molecules; the reaction is catalyzed by enzymes called DNA methyltransferases that are specific for nucleotide and position of methylation. In eukaryotes, methylation is involved in gene expression, and plays a role in a variety of epigenetic mechanisms, including development, X chromosome inactivation, genomic imprinting, mutability of DNA, and uncontrolled cell growth in cancer. The term "X chromosome inactivation" refers to the inactivation of one of each pair of X chromosomes to form the Barr body in female mammalian somatic cells. Thus tissues whose original zygote carried heterozygous X borne genes should have individual cells expressing one or other but not both of the X encoded gene products. The inactivation is thought to occur early in development and leads to mosaicism of expression of such genes in the body.

Embryonic Stem (ES) Cells: Pluripotent stem cells derived from the inner cell mass of the blastocyst that proliferate in vitro. Human embryos reach the blastocyst stage 4-5 days post fertilization, at which time they consist of 50-150 cells. ES cells. Because of their plasticity and potentially unlimited capacity for self-renewal, ES cell therapies have been proposed for regenerative medicine and tissue replacement after injury or disease. In some embodiments, ES cells can be produced from culturing the inner cells mass of a blastocyst and culturing these cells on fibroblasts in the presence of mitomycin-C in serum containing medium. These cells can form embryoid bodies.

Epigenetic: A heritable change in gene expression or cellular phenotype caused by mechanisms other than changes in a DNA sequence. Examples of such changes are DNA methylation and histone modification. Method of detecting such modifications are disclosed, for example, in U.S. Pat. Nos. 5,625,105; 6,300,071; 6,569,684; 7,035,739; 7,037,650; and 7,144,701.

Fetal cells: Cells from a fetus. In several embodiments, fetal cells are present in vaginal fluid collected from a pregnant female. The fetal cells present in the vaginal fluid can be isolated from maternal cells also present in the vaginal fluid.

Fetus: Unborn offspring of a female mammal more than 8 weeks after conception.

Genomic or epigenetic characteristic associated with a biological outcome: A genetic characteristic or epigenetic characteristic that results in, or is correlated with, a phenotype of a subject. The genetic characteristic can be the presence or absence of all or a portion of a chromosome (e.g., an aneuploidy) or the presence or absence of a genetic mutation, that is associated with a particular biological characteristic, such as sex or disease state. Similarly, an epigenetic characteristic can be a heritable change in gene expression or cellular phenotype, caused by a mechanism other than changes in a DNA sequence, that is associated with a particular biological characteristic, such as sex or disease state.

Intralabial Pad: Absorbent pad designed to be placed longitudinally between the vaginal lips or labia, and are particularly useful to absorb vaginal discharges.

Invasive Collection of Fetal Cells: A procedure that involves penetration of the cervix, biopsy, or penetration the skin (such as with a needle), of a pregnant female for the collection of fetal cells. Amniocentesis, chorionic villus sampling, and transcervical cell collection are examples of invasive methods of fetal cell collection. A "non-invasive" method for collecting cells does not involve penetration of the cervix, biopsy, or penetration of the skin of a subject for cell collection. The collection of cells by placing an absorbent medium in an interlabial or intravaginal space or adjacent to the perineum at the vaginal opening of the pregnant female, and isolating cells from the absorbent medium is a non-invasive method of collection fetal cells.

Isolated Cells or Purified Cells: As used herein, the term "isolated cells," "purified cells," "isolated cell population," "purified cell population" refers to a preparation of one or more cells, such as fetal cells, that has been manipulated to provide a preparation of cells that is substantially free of additional components, such as maternal cells. In some embodiments, the fetal cells are at least about 70%, by weight or number, free from other components that are present when the cell is produced, such as other types of cells (e.g., maternal cells). In various embodiments, the cell is at least about 75%, or at least about 85%, or at least about 90%, or at least about 95%, or at least about 99%, by weight or number, pure, from maternal cells. A purified cell preparation can be obtained, for example, by purification (e.g., extraction) using fluorescence-activated cell-sorting or magnetic bead affinity purification, or other techniques known to the skilled artisan. Purity can be assayed by any appropriate method, such as fluorescence-activated cell-sorting (FACS) or by visual examination.

Larger and smaller portions: The major portion of the pad is a larger portion, and a minor portion is a smaller portion. Large and small can be defined, for example, in terms of cross-sectional area, volume, or transverse dimension. In some embodiments, the pad is inserted between the labia with the minor portion as the leading edge inserted, in which example the minor portion would also be considered an anterior edge and the major portion would be a posterior portion.

Medicinal Agent: A therapeutic agent for treatment of the interlabial space, perivaginal region, vagina, and/or for delivery or for cell preservation. Specific, non-limiting examples of a medicinal agent are anesthetics, lubricants or preservatives.

Totipotent, Pluripotent, Multipotent Stem Cells: As used herein, the term "totipotent" or "totipotency" refers to a cell's ability to divide and ultimately produce an entire organism including extra-embryonic tissues in vivo. In one aspect, the term "totipotent" refers to the ability of the cell to progress through a series of divisions into a blastocyst in vitro. The blastocyst comprises an inner cell mass (ICM) and a trophoblast. The cells found in the ICM give rise to pluripotent stem cells (PSCs, see below) that possess the ability to proliferate indefinitely, or if properly induced, differentiate in all cell types contributing to an organism. Trophoblast cells generate extra-embryonic tissues, including placenta and amnion.

Totipotent Stem cells (TSCs) are the source of PSCs. As used herein, the term "pluripotent" refers to a cell's potential to differentiate into cells of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent stem cells can give rise to any fetal or adult cell type including germ cells. However, PSCs alone cannot develop into a fetal or adult animal when transplanted in utero because they lack the potential to contribute to extra-embryonic tissue (e.g., placenta in vivo or trophoblast in vitro).

PSCs are the source of multipotent stem cells (MPSCs) through spontaneous differentiation or as a result of exposure to differentiation induction conditions in vitro. The term "multipotent" refers to a cell's potential to differentiate and give rise to a limited number of related, different cell types. These cells are characterized by their multi-lineage potential and the ability for self-renewal. In vivo, the pool of MPSCs replenishes the population of mature functionally active cells in the body. Among the exemplary MPSC types are hematopoietic, mesenchymal, or neuronal stem cells. "Committed progenitors" give rise to a fully differentiated cell of a specific cell lineage. Exemplary lineages include pancreatic cells, epithelial cells, cardiac cells, endothelial cells, liver cells, endocrine cells, and the like.

Trophoblast: The outermost layer of cells of the embryo of placental mammals that attaches the fertilized ovum to the uterine wall. Trophoblasts play an important role in embryo implantation and interaction with the decidualised maternal uterus. The core of placental villi contain mesenchymal cells and placental blood vessels that are directly connected to the fetal circulation via the umbilical cord. This core is surrounded by two layers of trophoblast; a single layer of mononuclear cytotrophoblast that fuse together to form the overlying multinucleated syncytiotrophoblast layer that covers the entire surface of the placenta. It is this syncytiotrophoblast that is in direct contact with the maternal blood that reaches the placental surface, and thus facilitates the exchange of nutrients, wastes and gases between the maternal and fetal systems.

Vaginal fluid: Aqueous solution secreted or discharged from the vagina. Vaginal fluid can include cells. Vaginal fluid from a pregnant female can include maternal cells and cellular components, as well as fetal cells and fetal cellular components. For example, the fetal cells can be somatic cells, embryonic stem cells, fetal stem cells or trophoblasts. In some embodiments, the fetal cells can be totipotent, multipotent or pluripotent stem cells.

Vaginal orifice: The opening of the vagina at the perineum.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

II. Collecting Fetal Cells and/or Cellular Components

Methods are provided herein for the collection of fetal cells and/or components of fetal cells. These methods include placing an absorbent medium in an interlabial or intravaginal space or adjacent to the perineum at the vaginal opening of a pregnant female and collecting vaginal fluid comprising cells and/or cellular components in the absorbent medium while the absorbent medium is in the interlabial or intravaginal space or adjacent to the perineum at the vaginal opening. The fetal cells and/or cellular components can be collected at any time during gestation, including during the first, second and third trimester. In some embodiments, the fetal cells and/or cellular components are collected in the absence of rupture of the amniotic sac. In other embodiments, the fetal cells and/or cellular components are collected without collecting maternal blood.

These methods allow fetal cells to be obtained without invasion of the cervix. Thus, transcervical sampling is not utilized. In some embodiments, the pregnant female has an intact amniotic sac. In other embodiments, the pregnant female has a rupture in the amniotic sac.

The fetal cells can be any cells of interest, including somatic cells, embryonic stem cells, fetal stem cells or trophoblasts. The fetal cells can be totipotent, multipotent or pluripotent stem cells. The cellular components can be any of the biological components of a cell, including, but not limited to DNA, RNA, proteins and lipids.

The absorbent medium can be used in the form of an interlabial pad, sanitary napkin or panty-liner. The retention of an interlabial pad in the interlabial space, or the use of a sanitary napkin or panty-liner, permits sustained contact between the pad and the vaginal orifice, for collection of fluids and fetal cells. Similarly a tampon can be retained in the vaginal canal for a sufficient time for the collection of fluids and fetal cells. In some embodiments, the pad is retained for a period of time that is sufficient for the collection of fetal cells, such as about 2 hours to about 10 hours, such as about 2 to about 8 hours, such as about 4 to 6 hours. In some specific non-limiting examples, the pad (or tampon) is retained such as about 2, about 3, about 4, about 5, about 6, about 7, about 8, about 9, about 10, about 11, or about 12 hours. The absorbent medium can have an inner core and an outer covering, wherein the outer covering has a visible matrix of pores of sufficient size to allow fetal cells to enter the pores. In some embodiments, the pores are at least 10 µm in diameter, such as about 10 µm to about 20 µm in diameter. In some embodiments, this is configured for intravaginal or interlabial placement.

In some embodiments, the methods utilize an interlabial pad. Various forms of interlabial pads, as well as methods of producing them, are described in U.S. Pat. Nos. 3,983,873; 4,095,542; 4,142,476; 4,995,150; 5,575,047; 5,727,481; 6,007,498; 6,183,455; 6,811,549; which are all incorporated herein by reference. These pads are designed to be placed longitudinally between the vaginal lips or labia, and are particularly useful to absorb light discharges of menstrual fluids, mid-cycle spotting or discharges, slight loss of urine caused by physical stress, or leakages following intercourse. In some embodiments, a biodegradable interlabial pad is utilized. The biodegradable pad is capable of being decomposed by natural biological processes.

Another example of an interlabial pad suitable for use with the present method is the absorbent interlabial device disclosed in U.S. Pat. No. 5,968,026, which issued to the Procter & Gamble Company, and which is incorporated by reference herein. A commercially available example of this pad is the Envive Miniform.

However, the invention is not limited to these specific particularly disclosed embodiments, which are only given by way of illustration. Any configuration of the pad is possible, which allows it to be capable of being substantially retained in the interlabial space by engagement with the labial folds, but can be simply and easily removed by manually removing it.

Figure 37A:
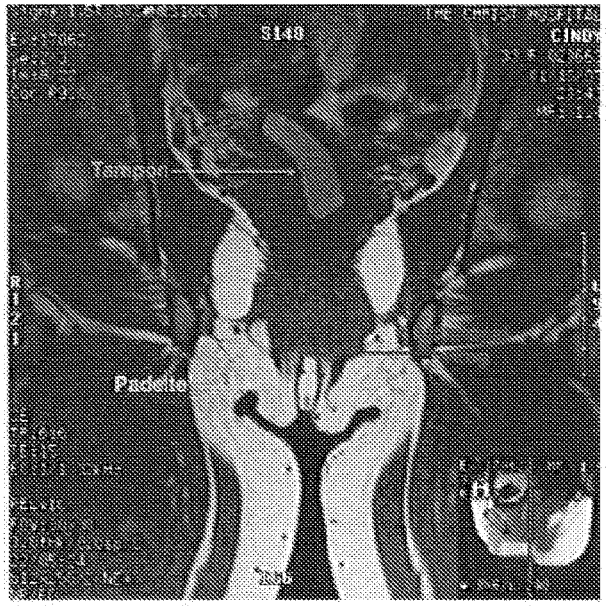
FIG. 37A is an MRI of an external feminine hygiene pad in place against the external female genitalia.
Figure 37B:
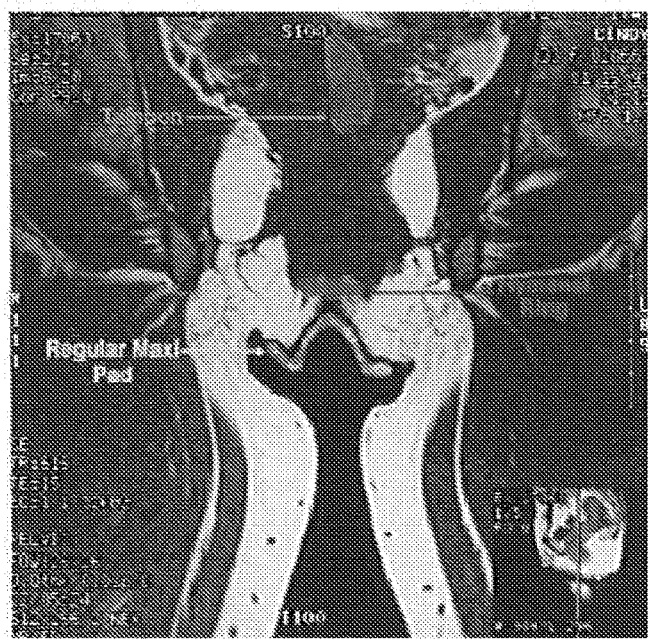
FIG. 37B is an MRI of an example of a pad in accordance with the present disclosure, in which the pad is retained between the labia, external to the hymenal ring.

The interlabial pad is positioned such that the pad is retained between the labia external to the subject's vagina. The anterior portion of the pad is designed for insertion of the pad between the subject's labia in the anatomic interlabial space adjacent to the vaginal orifice, and the posterior portion is retained between the labia without the need for adhesive or other attachment devices, as in FIG. 37B. Alternatively, a portion of the pad can project into the vagina, for example to improve retention and enhance cell collection.

The interlabial pad can be any of a variety of shapes, and particularly shapes which taper toward an anterior or leading edge of the pad. The anterior edge is often sufficiently wide to be retained outside the vaginal orifice, but can be sufficiently narrow to extend at least partially within the vagina (for example no more than 1 inch into the vagina, and in some examples less than ½ inch). When the pad is substantially or completely retained external to the vagina, the posterior edge impinges against the surrounding labia to retain the pad in place. The pad can be symmetric or asymmetric, rounded or elongated, tapering or non-tapering, folded or not folded. However, particular embodiments taper from a relatively larger posterior portion to a relatively smaller anterior portion. The enlarged posterior portion is often large enough to at least slightly deform the surrounding labia to improve frictional engagement between the labia and the pad. The relatively small anterior portion may in some examples be closer to the width of the vaginal orifice, and is more comfortably retained in the narrow interlabial space adjacent the vaginal orifice. The pads with a bipartite structure (with a major and minor portion) further enhance the comfort and retention of the pad. The approach disclosed herein is non-invasive route (for example, avoiding the risks of transcervical collection).

Figure 6:
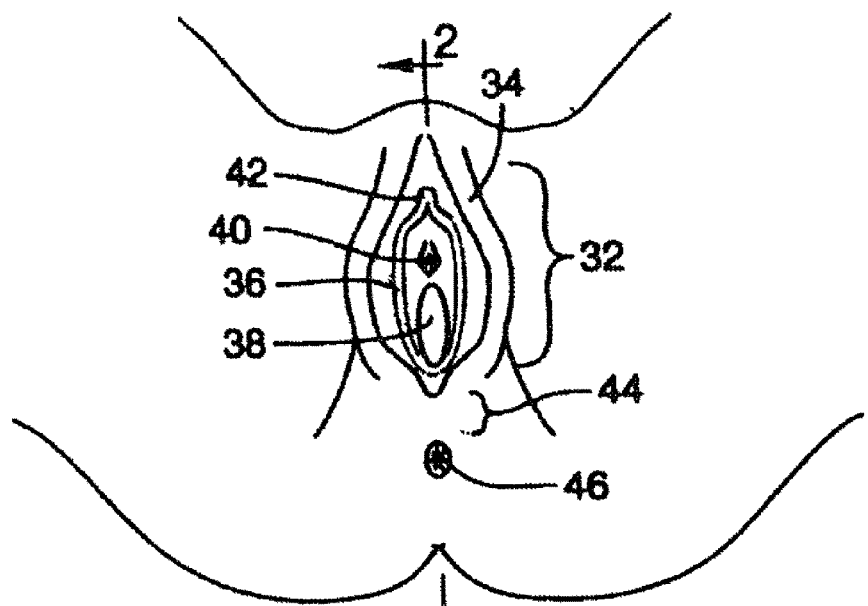
FIG. 6 is a schematic view of the perineum and thighs, which illustrates the external female genitalia.
Figure 7:
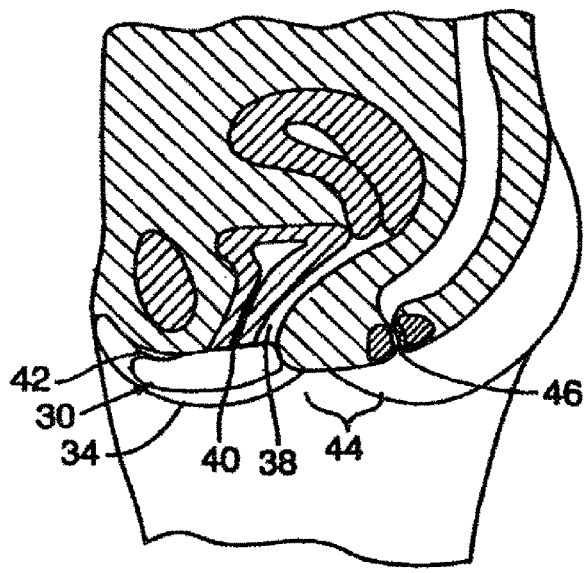
FIG. 7 is a cross-sectional sagittal view taken along line 2-2 of FIG. 1, but showing a pad positioned between the labia.
Figure 8:
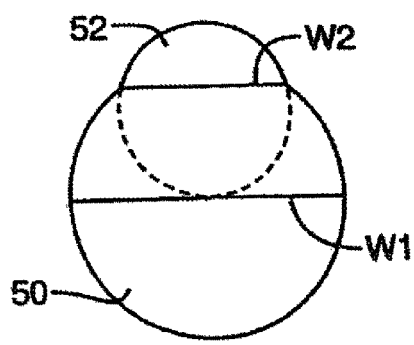
FIG. 8 is a schematic view of one embodiment of the interlabial pad.

An embodiment is shown in FIGS. 6-8. FIG. 6 illustrates the urogenital anatomy of a female. Interlabial space 32 is approximately bounded by the labia majora 34. Anatomical structures found within the interlabial space include the labia minora 36, vaginal orifice 38, urethral orifice 40, and clitoris 42. The perineum is a term that often refers to the pelvic outlet that gives passage to the urogenital ducts and anus, but it is used herein n a more restricted sense to refer to the area 44 which lies between interlabial space 32 and the anus 46. A perineal pad abuts against at least a portion of the perineum.

FIG. 7 is a sagittal section of female urogenital anatomy, and illustrates that in this embodiment of the invention, interlabial pad 30 is positioned in interlabial space 32 approximately adjacent labia majora 34, vaginal orifice 38, and urethral orifice 40.

In the embodiments disclosed in FIGS. 7-8, interlabial pad 30 is an elongated absorbent member, for example made of cotton, and has a bipartite profile with a major portion 50 and a minor portion 52. In the illustrated example, the major and minor portions each have a cross section that is a portion of a circle, where the portion of the circle of the major portion 50 has a greater diameter than the portion of the circle of the minor portion 52. The curvature of the minor portion is greater than the curvature of the major portion. The overall shape of pad 30 therefore includes a rounded major portion and a rounded minor portion, in which the transverse diameter or width W1 (FIG. 8) of the major portion is greater than the transverse diameter or width W2 of the minor portion, so that the width of pad 30 tapers in the direction of minor portion 52.

The width of major portion 50 is sufficient to fit comfortably and be retained without adhesives within the interlabial space. Minor portion 52 has a reduced width (and increased taper) to minimize pressure and discomfort in the area of vaginal and urethral orifices 32. The minimum width of minor portion 52 is, in some embodiments, substantially the same or slightly less than the maximum diameter of vaginal orifice 38. The outer profile of both the major and minor portions may be arcuate to help conform to surrounding body tissues. The cross-sectional area of minor portion 52 in some embodiments is less than 50% of the cross-sectional area of pad 30, and has a cross-sectional area that is, for example, 10 to 49% of the total cross-sectional area of pad 30.

The reduced width of minor portion 52 makes interlabial pad 30 easy to insert and use. Labia majora 34 and labia minora 36 are spread apart either by moving them apart, or by introducing the reduced width minor portion 52 as a leading edge of the pad between them, and advancing the pad toward vaginal orifice 38. As pad 30 is inserted into interlabial space 32, the leading minor portion 52 gradually moves labia majora and labia minora apart, to facilitate acceptance of major portion 50. Once minor portion 52 is in place against vaginal orifice and urethral orifice 32, major portion 50 provides an enlarged retention member that frictionally engages surrounding portions of labia majora 34 to retain interlabial pad 30 in position.

The pad is easily inserted between the labia majora and is easily retained in the interlabial space without the need for auxiliary retaining means. Thus, a light pressure on the major portion 50 will cause the smaller minor portion 52 to open the labia majora slightly and allow pad 30 to take its proper position in the interlabial space. The radii of the respective portions are such that the interlabial space 36 is substantially or completely occupied by the pad. The elongated pad extends along the interlabial space, such that the length of the pad helps frictionally engage the pad and enable it to resist dislodgement so that fetal cells can be collected.

Some other examples of alternative embodiments of the pad with a tapering portion are shown in FIGS. 9-34. Many of these embodiments are shown in cross-section as relatively flat, although they can be elongated (as indicated by the fragmentary depiction in each Figure).

In the embodiment shown in FIG. 9, a one piece absorptive pad 58 has a "tear-drop" or ovoid cross sectional shape which tapers progressively to a leading anterior edge portion 60 of limited transverse dimension from a posterior portion 62 of relatively large transverse dimension. The pad 58 may be elongated transverse to the illustrated cross-section, or it may not be elongated (such that the length of the pad transverse to the cross section is less than the anterior-posterior dimension A-P of the cross-section). In elongated embodiments, the pad may be of uniform cross section along the length thereof, or may be tapered from one end to the other end thereof, and in particular embodiments, is tapered in its anterior-posterior dimension AP. The user may readily and quickly insert the pad 58 into the interlabial space by introducing leading anterior portion 60 into the interlabial space. The pad is firmly self retained in the space and exhibits substantial absorptive capacity for vaginal fluid and fetal cells, and resists accidental dislodgement from the interlabial space.

Other embodiments of the pad are shown which have posterior major portions of a polygonal (for example quadrilateral) shape, such as rectangular or square. Thus, as shown in FIG. 10, pad 62 includes a posterior portion 64 having flat bottom and side surfaces; and the anterior minor portion 66 has surfaces 68 which incline toward one another toward a leading edge 70. Anterior portion 66 therefore forms a wedge that parts the labia as it is introduced between them.

FIG. 11 shows a pad 72 that includes a posterior portion 74 of substantially square cross section; and a fingerlike anterior portion 76 of limited transverse dimension, which is much narrower than the corresponding transverse dimension of posterior portion 74. The juncture 78 of portions 74, 76 forms an essentially flat shoulder that extends transverse to the anterior-posterior dimension AP. In the disclosed embodiment, the anterior-posterior dimension of anterior portion 76 is substantially the same as the anterior-posterior dimension of posterior portion 74. The slender projecting finger of this pad can be configured to project through the vaginal orifice and into the vagina when the interlabial pad is in place. As discussed in detail below, the projecting finger can carry an agent designed to increase cell viability. In some embodiments, the projecting figure includes a non-toxic core material, such as, but not limited to, rayon.

FIG. 12 shows a pad 80 that is similar to that of FIG. 11, except that the sides of anterior portion 84 diverge away from top edge 86, to present a more tapered profile. FIG. 13 shows a pad 88 having a posterior portion 90 and an anterior portion 92, wherein both portions are substantially quadrilateral in shape, except for a sloping flat shoulder 94 at the juncture of portions 90, 92. FIG. 14 shows a pad 95 that includes a posterior portion 96 of quadrilateral shape and an anterior portion 98 having upwardly converging side surfaces 100 and a flat leading edge 102.

While the pads shown in FIGS. 10-14 have posterior portions with flat bottom surfaces, the bottom surfaces may have other configurations. Thus, as shown in FIG. 15, the posterior portion P has an arcuate bottom surface A, while in FIG. 16, the posterior portion P' has converging surfaces C and an arcuate bottom edge B.

Further, alternative embodiments are shown in FIGS. 17 and 18. Thus, in FIG. 17, the non-bipartite pad 104 is of generally triangular cross section, with a posterior portion 106 of large cross section and an anterior portion 108 of small cross section. The pad 104 has flat, converging surfaces 110, a slightly curved bottom surface 112, rounded bottom edges 114 and a rounded leading edge 116. The pad 118 shown in FIG. 18 is similar to pad 106, except that the anterior portion 120 is transversely constricted and provides a linear juncture J between posterior portion 122 and anterior portion 120. This is an example of a bipartite pad that has major and minor portions.

FIG. 19 shows pad 124, which includes a posterior portion 126 of substantially hexagonal cross section and a transversely constricted anterior portion 128 with a rounded leading edge 130. The surfaces of posterior portion 126 are flat and edges thereof may be rounded.

FIG. 20 shows pad 132, which includes a posterior major portion 134 defined by opposed convergent flat surfaces 136 and a slightly rounded bottom surface 138; while anterior minor portion 140 is of a triangular cross section.

The pads may be suitably tapered in a longitudinal direction transverse to the AP direction. Thus pad 142, as shown in FIG. 21, has its anterior portion 144 and posterior portion 146 tapered in respect of both the longitudinal and transverse axes thereof; whereas in pad 148, as shown in FIG. 22, anterior portion 150 and posterior portion 152 are tapered longitudinally only.

FIG. 23 shows yet another embodiment of the pad 154, in which the anterior portion 156 and posterior portion 158 are substantially ovoid in cross-section, with the transverse width of anterior portion 156 much less than the transverse width of posterior portion 158.

The pads may be further modified, as shown in FIGS. 24-26. Thus, as shown in FIG. 24, the pad 160 has its posterior portion 162 sloped at one end as at 164, to make the pad conform to the anatomy of the user. Alternatively, as shown in FIG. 25, the pad 166 may be sloped at both opposite ends 168, 168'. Alternatively, as shown in FIG. 26, pad 170 has its posterior portion 172 sloped at opposite ends in a convergent configuration. If desired, in the foregoing embodiments, the anterior portions of the pads may also be sloped to converge toward one another. FIG. 27 shows an embodiment of a pad 174 that has an anterior portion 176 and posterior portion 177. The posterior portion 177 is formed with a longitudinal groove 178 of normally triangular section, forming wings 180. When the pad 174 is inserted into the interlabial space, as shown in FIG. 28, the wings 180 are resiliently urged toward each other and bear against the labia majora, thereby increasing the retention of the pad within the interlabial space.

The various forms of pads set forth above may also include the groove in the anterior portions thereof. The pads set forth above which have opposed flat surfaces (e.g. FIGS. 11-14), are particularly adapted to conform to the medial surfaces of labia majora, for retention and cell collection. Such embodiments that have slender projecting anterior portions can also be configured such that the anterior projection inserts into the vaginal opening, to further enhance retention of the pad.

Although some of the pads have been shown to taper longitudinally from one end to the other end, they may also taper from a central portion to the opposite ends thereof. Thus, while the pad may be of uniform cross section throughout its length, it may also have a tapered form. In this configuration, no string or other removal aid is required, and the pad can be removed manually, such as with a gentle tap.

Another embodiment of the interlabial pad 182 is shown in FIG. 29, in which the pad 182 has a posterior portion 184 and anterior portion 186, each having a cross section that defines a portion of a circle. Each of the posterior and anterior portions is a portion of a sphere that is symmetric in all directions with respect to a center point, and has a constant radius. For example, posterior portion 184 is symmetric with respect to center C1, while anterior portion 186 is symmetric with respect to center C2.

FIG. 30 shows yet another embodiment of a pad 188 having merged portions 190, 192 which are of part elliptical cross section; the portion 190 having major and minor axes somewhat larger then those of portion 192, which also lends itself to easy insertion and removal. Portion 190 is symmetric in all directions with respect to perpendicular planes of symmetry, one of which is shown as P in FIG. 30. In this embodiment, the pad is not elongated in any direction, although in other embodiments longitudinal elongation is possible.

The pad 194, shown in FIG. 31, is of an elliptical cross section. This embodiment lacks a major portion and a minor portion, and instead has a cross-section that is completely symmetric with respect to an anterior-posterior plane AP. In use, pad 194 is inserted along the AP axis into the interlabial space (either narrowed end of the pad can be the leading edge of insertion).

The pad 200 shown in FIG. 32 is an elongated version of the pad in FIG. 30, which has a more spherical configuration. Pad 200 in FIG. 32 is initially of a round cross section, but is formed into a larger and smaller portion by using a mechanical binding agent, such as thread or heat welding, similar to that described in Gerstenburger (U.S. Pat. No. 5,575,047). Alternatively, it can be sewn along the junction between the two portions with biodegradable thread, so that the pad is completely biodegradable, and can be flushed down a toilet. Biodegradable pads can be made by any method, such as those disclosed in U.S. Pat. No. 5,575,047, which is incorporated herein by reference.

In certain examples, the absorbent pads are additionally (or alternatively) impregnated with selected scents, to provide a soothing and pleasant odor. In one embodiment, the pad is impregnated with cell preservation agents in the anterior (or minor) portion only (that fits closest to the vaginal opening), or in the posterior portion only. In other embodiments, both the anterior (or minor) and posterior (or major) portions are impregnated with cell preservation agents. Alternatively, the anterior portion may be impregnated with medication, and the posterior portion is impregnated with an agent, or vice versa. These include, but are not limited to, hexamidine or zinc oxide (ZnO).

In one embodiment, the pad includes a groove in the anterior or posterior portion, and the scent, preservative, or another agent is added within the groove or impregnated in the pad adjacent to the groove. However, in other embodiments an agent is introduced into the pad by applying it as a liquid or powder to the pad. Thus, active agents can be introduced on to the surface of the pad, impregnated throughout it, or introduced into superficial regions of the pad, or parts of it.

FIG. 33 shows a cross-section of an embodiment of an elongated absorbent pad 200 that has been modified to carry agents for cell preservation. The principles of the elongated embodiment could, however, be adapted to the non-elongated embodiments of the type shown in FIG. 29. In the embodiment shown in FIG. 33, pad 200 includes posterior portion 202 and anterior portion 204, which is formed with a groove 206 extending longitudinally along the top of anterior pad portion 204. The groove is prefilled with a material 208, for example, with an ointment, preservatives, lubricants, buffers and the like. Placing the interlabial pad in the interlabial space, with anterior portion 204 adjacent to the vaginal orifice and urethral orifice, causes the normal transverse constriction of the pad 200 (and particularly compression of anterior portion 204) to dispense materials, which have a suitable viscosity, to the interlabial space.

It has been found that the curvilinear surface portions and the non-uniform cross sections of the several pads shown herein are highly effective in positioning the pad in the interlabial space and retaining it in place. Further, there is no tendency to uncomfortably force the labia majora apart or to exert undue pressure against their wall portions.

Figure 34:
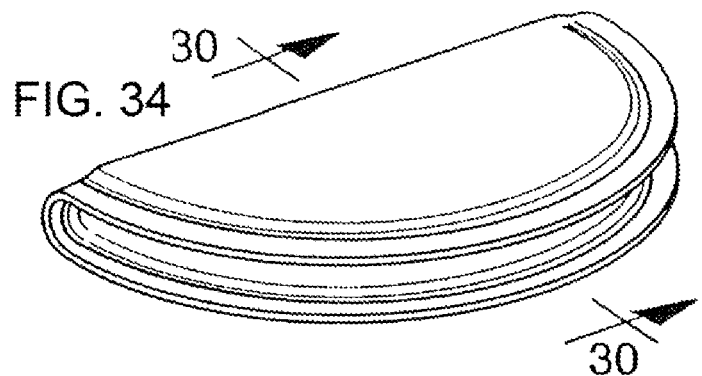
FIG. 34 is a perspective view of an elongated folded pad.
Figure 35:
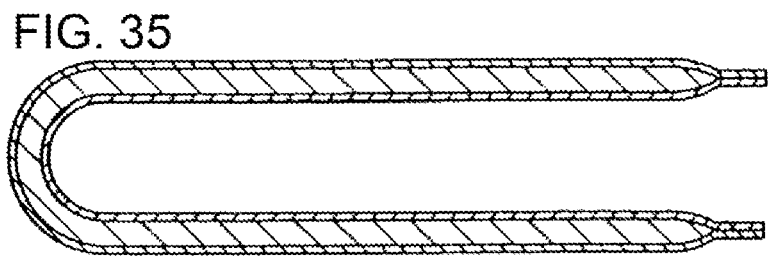
FIG. 35 is an end view of the pad of claim 29.
Figure 36:
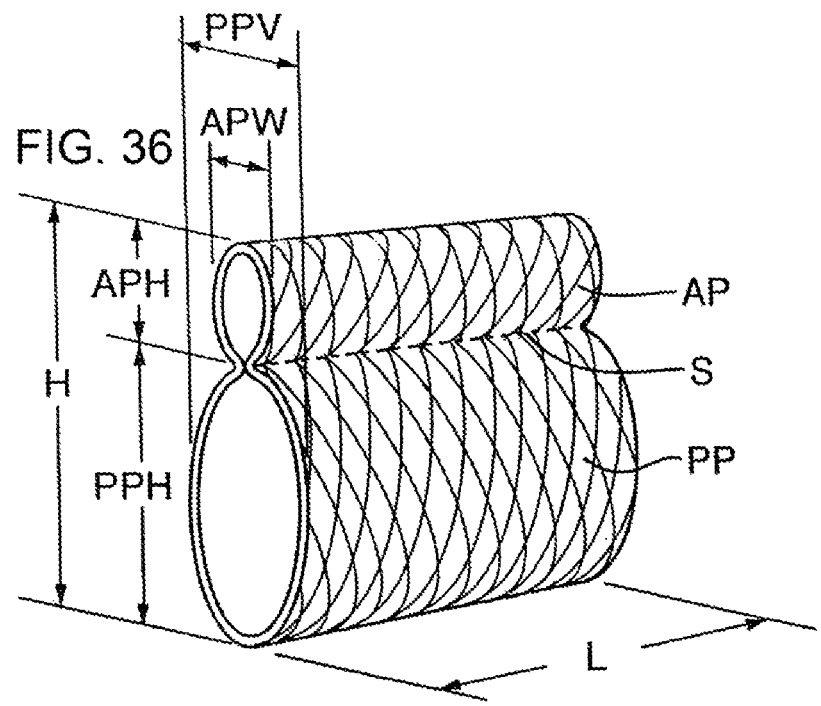
FIG. 36 is a perspective view of an elongated pad.

FIG. 34 shows a particular embodiment wherein an interlabial pad is formed of a polypropylene or polyester nonwoven fabric with a rayon sliver core. As shown in FIG. 30, the interlabial pad has an overall length L of about 15 to about 75 mm, and an overall height H of about 19 to about 22 mm. Of the overall height of the interlabial pad, the anterior portion AP of the interlabial pad has a height APH of about 4 to about 7 mm. The posterior portion PP of the interlabial pad has a height PPH of about 12 to about 18 mm. In addition, posterior portion PP of the pad has a width PPW of about 8 to about 10 mm. Anterior portion AP has a width APW less than width PPW of posterior portion PP of the pad. In one specific, non-limiting example, width PPW of posterior portion PP of the interlabial pad is from about 4 to about 7 mm. The posterior portion PP of the pad is demarcated from anterior portion AP of the pad by stitching S. In one specific, non-limiting example the stitching is standard 401 chain stitch of about 8-10 SPI.

In particular embodiments, the pad is formed of a soft absorptive material such as rayon, cellulose, cotton, or another suitable natural or synthetic fiber or sheeting. In one embodiment the pad is flushable, and can be made of biodegradable material. In some embodiments, the absorbent medium comprises an inner core and an outer covering, the outer covering having a visible matrix of pores of sufficient size to allow cells to enter the pores. The pad may be made as described in U.S. Pat. No. 5,575,047, herein incorporated by reference.

While interlabial pads are of use, they are not the only means of cell collection. In some embodiments, a device placed intravaginally collects fetal cells and/or components of fetal cells. Devices can be used such as those disclosed in U.S. Pat. Nos. 6,174,293 and 5,725,841, which is incorporated herein by reference. In addition, absorbent medium in the form of a tampon can be used, such as those disclosed, for example, in U.S. Pat. Nos. 7,713,253; 7,341,737; 7,091,395; 6,743,212; or 6,155,990, which are incorporated herein by reference. In further embodiments, sanitary napkins or panty-liners can be utilized for the collection of fetal cells. These include a variety of sanitary napkins that are commercially available, such as, but not limited to, those produced by UNICHARM®.

III. Separation of Maternal and Fetal Cells and Cellular Components

In some embodiments, after fluid and cells are collected on an absorbent medium, such as an interlabial pad, sanitary napkin, tampon or panty-liner, the cells and/or cellular components can be extracted from the absorbent medium. This can involve placing the absorbent medium into a liquid that retains the viability of the cells, such as a tissue culture medium or physiological buffer, such as a buffer with a pH of about 7 to about 7.6, such as about 7.2 to about 7.4, such as about 7.2, about 7.3 or about 7.4. The release of the cells and/or cellular components from the absorbent medium can include shaking, vibration, light sonication, or any method which allows the release of the cells and/or cellular components but retains cell viability. In one non-limiting example, the absorbent medium is agitated for about 1 to about 30 minutes, such as for about 2 to about 5 minutes, in the presence of a physiological buffer, such as phosphate buffered saline or Dulbecco's modified Eagle's medium.

Following release of cells and/or cellular components, the tissue culture medium or physiological buffer can then be centrifuged to form a pellet of cellular material. This cellular material can be resuspended at a desired concentration in an additional portion of a medium or physiological buffer. In some embodiments, a cell suspension is produced from the cell pellet for further propagation of the cells. In other embodiments, cellular components are extracted from the cellular material.

In further embodiments, the supernatant is collected following centrifugation to form a pellet of cellular material. This supernatant includes cellular components, such as DNA, RNA, proteins and/or lipids. The cellular components then can be isolated using methods known to those of skill in the art. For example, the extraction of fetal DNA and RNA from maternal samples is disclosed in U.S. Published Patent Application No. 20120108460; these methods are also of use with regard to the supernatant. For example, genomic DNA can be isolated using a QIAGEN® Kit for purification of DNA from blood cells, following the manufacturer's instructions (for example, QIAmp DNA Blood Midi Kit, Catalog number 51183).

Once obtained, the sample of cells and/or cellular components can be stored at room temperature until use. In other embodiments, the sample can be stored at 0 to 4° C. until use. The sample can be transported and/or stored at 4° C. For long-term storage, the sample can be stored in at −80° C. In one embodiment, when cells are collected and/or stored the medium comprises serum such as bovine calf serum or human serum. In some examples, GIBCO® AMNIOMAXII™, GIBCO® AMNIOMAX™ C-100, or GIBCO® keratinocyte-serum free media supplemented serum can be used. In a further embodiment, the medium is degassed with nitrogen to reduce oxidative stress to the samples.

In some embodiments, when cells are to be analyzed, fetal cells are separated from maternal cells, in order to isolate the fetal cells. This can be accomplished by a variety of methods including, for example, fluorescence activated cells sorting (FACS). Fetal cells can be positively and/or maternal cells can be negatively selected, using a variety of techniques well known in the art, including cell sorting, especially FACS, by using an affinity reagent bound to a substrate (e.g., a plastic surface, as in panning), or by using an affinity reagent bound to a solid phase particle which can be isolated on the basis of the properties of the solid phase particles for example beads (e.g., colored latex beads or magnetic particles). The procedure used will depend on whether maternal or fetal cells are being selected and how the cells have been labeled. For selection of cells by cell sorting, the cells are labeled directly or indirectly with a substance which can be detected by a cell sorter, preferably a dye. The dye can be a fluorescent dye. A large number of different dyes are known in the art, including fluorescein, rhodamine, Texas red, phycoerythrin, and the like. Any detectable substance, which has the appropriate characteristics for the cell sorter, may be used (e.g., in the case of a fluorescent dye, a dye which can be excited by the sorter's light source, and an emission spectra which can be detected by the cell sorter's detectors).

For the selection of cells from a sample using solid-phase particles, any particle with the desired properties may be utilized. For example, large particles (e.g., greater than about 90-100 μm in diameter) may be used to facilitate sedimentation. Preferably, the particles are "magnetic particles" (i.e., particles which can be collected using a magnetic field). Typically, maternal cells labeled with the magnetic probe are passed through a column, held within a magnetic field. Labeled maternal cells are retained on the column (held by the magnetic field), while unlabeled fetal cells pass straight through and are eluted at the other end. Magnetic particles are now commonly available from a variety of manufacturers including Dynal Biotech (Oslo, Norway) and Miltenyi Biotech GmbH (Germany). An example of magnetic activated cell sorting (MACS) is provided in U.S. Pat. No. 4,675,286. Laser-capture micro-dissection can also be used to select labeled cells. Methods of using laser-capture microdissection are known in the art (see, for example, U.S. Published Patent Application No. 2003/0227611).

In flow cytometry, a beam of laser light is projected through a liquid stream that contains cells, or other particles, which when struck by the focused light give out signals which are picked up by detectors. These signals are then converted for computer storage and data analysis, and can provide information about various cellular properties. In some embodiments, forward scatter data can be used to select and/or enrich fetal cells, either multinucleated and/or non-multinucleated, based on cell size. For example, when a laser hits the cell, the larger the cell the more photons of light it scatters. By measuring the light scattered on the side of a cell furthest from where the laser hits the cell, a measure of cell size can be obtained, and fetal cells of a particular size can be isolated.

Many larger flow cytometers are also "cell sorters", such as fluorescence-activated cell sorters (FACS), and are instruments, which have the ability to selectively deposit cells from particular populations into tubes, or other collection vessels. In an embodiment, the cells are isolated using FACS. This procedure is well known in the art and described by, for example, Melamed, et al. Flow Cytometry and Sorting Wiley-Liss, Inc., New York, N.Y. (1990); Shapiro Practical Flow Cytometry, 4 ed, Wiley-Liss, Hoboken, N.J. (2003); and Robinson et al. Handbook of Flow Cytometry Methods Wiley-Liss, New York, N.Y. (1993); Harkins and Galbraith (1987) and U.S. Pat. No. 4,765,737.

In order to sort cells, the instrument's electronics interprets the signals collected for each cell as it is interrogated by the laser beam and compares the signal with sorting criteria set on the computer. If the cell meets the required criteria, an electrical charge is applied to the liquid stream, which is being accurately broken into droplets containing the cells. This charge is applied to the stream at the precise moment the cell of interest is about to break off from the stream, then removed when the charged droplet has broken from the stream. As the droplets fall, they pass between two metal plates, which are strongly positively or negatively charged. Charged droplets get drawn towards the metal plate of the opposite polarity, and deposited in the collection vessel, or onto a microscope slide, for further examination.

The cells can automatically be deposited in collection vessels as single cells or as a plurality of cells, such as using a laser, for example an argon laser (488 nm) and for example with a Flow Cytometer fitted with an Autoclone unit (Coulter EPICS Altra, Beckman-Coulter, Miami, Fla., USA). Other examples of suitable FACS machines useful for the methods of the invention include, but are not limited to, MOFLO® High-speed cell sorter (Dako-Cytomation Ltd), FACS ARIA® (Becton Dickinson), ALTRA® Hyper sort (Beckman Coulter) and CYFLOW® sorting system (Partec GmbH).

Fetal and maternal cells can be separated based on the expression of genes in the major histocompatibility complex (MHC). The MHC includes at least three classes of genes. Class I and II genes encode antigens expressed on the cell surface, whilst class III genes encode several components of the complement system. Classes I and II antigens are glycoproteins that present peptides to T lymphocytes. Human MHC molecules are also known in the art as Human Leukocyte Antigens (HLA). Thus, the terms "HLA" and "MHC" are often used interchangeably.

Human and murine class I molecules are heterodimers, consisting of a heavy alpha chain (45 kD) and a light chain, beta-2-globulin (12 kD). Class I molecules are found on most, if not all, nucleated cells. The alpha chain can be divided into three extracellular domains, alpha1, alpha2 and alpha3, in addition to the transmembranous and cytoplasmic domains. The alpha3 domain is highly conserved, as is beta-2-microglobulin. Both alpha3 domain and beta-2-microglobulin are homologous to the CH3 domain of human immunoglobulin. There are 3 class I loci (B,C,A) in the short arm of human chromosome 6, and 4 loci (K, D(L), Qa, Tla) in murine chromosome 17. These loci are highly polymorphic. The variable residues are clustered in 7 subsequences, 3 in alpha1 domain and 4 in alpha2 domain. There are three major human class II loci (HLA-DR, HLA-DO, HLA-DP). All class II beta chains are polymorphic. The human HLA-DQ alpha chain is also polymorphic.

Agents, such as an antibody that specifically bind an MHC molecule, can be used to isolate fetal and maternal cells. Generally, antibodies are of use that specifically bind an extracellular portion of the MHC molecule. In this manner, the method can be used to enrich live fetal cells. Furthermore, an additional step of ensuring that the agent passes through the cell membrane (for example having to fix and permeabilize the cell) is not required. In one embodiment, an antibody that specifically binds HLA-A, HLA-B and HLA-C molecule is utilized. In one embodiment, an antibody is utilized that specifically binds HLA-A or HLA-B molecules. More than one antibody can be used, wherein each antibody specifically binds a different classes or subclasses of MHC molecules. A "sub-class" of a MHC molecule is a distinct type of MHC molecules of a particular class.

Thus, the method can include i) contacting the cells with an antibody that specifically binds at least one MHC molecule, and ii) removing cells bound by the agent. More than one antibody, which specifically binds an MHC molecule can be used. For example, in an embodiment, the method comprises contacting the cells with i) an antibody that specifically binds a Class I MHC molecule, and ii) an antibody that specifically binds at least one Class II MHC molecule to separate fetal cells.

There are maternal cell specific markers that are not expressed on at least the majority of fetal cells. Those skilled in the art are aware that the types of nucleated maternal cells in maternal blood include B cells, T cells, monocytes, macrophages dendritic cells and stem cells, each characterized by a specific set of surface markers that can be targeted for depletion. Examples of non-MHC molecules, which can be targeted to possibly further deplete the sample of maternal cells include, but are not limited to, CD3, CD4, CD8, CD10, CD14, CD15, CD45, CD56. For example, magnetic beads can be produced which have both anti-MHC and anti-CD45 antibodies attached the bead, which can be then utilized for cell separation. Examples of maternal cells that may be depleted include, but are not limited to, vaginal epithelial cells, cervical epithelial cells, endometrial cells, maternal endothelial cells, maternal placental cells, polymorphs and mesenchymal cells of the placental villi.

Fetal cells can be positively selected by using agents, such as antibodies which specifically bind molecules, typically proteins, which are not significantly produced by maternal cells in the sample. Examples of fetal cell markers include, but are not limited to, molecules that are expressed by syncytiotrophoblasts and/or cytotrophoblasts, but is not expressed by maternal cells. Examples include, but are not limited to, NDOG1 (AbCam, GeneTex, Serotec), NDOG2, Human Chorionic Gonadotropin (Calbiochem), MCP/cd46 (trophoblast/lymphocyte cross-reactive protein) (Abnova), TPBG (Trophoblast glycoprotein) (Abnova), GCSF receptor, ADFP (Adipose Differentiation Related Protein) (GenWay), Apolipoprotein H (AbCam), Placental Alkaline Phosphatase (AbCam), CXCR6 (Chemokine receptor 6) (R&D Systems), HLA-G (AbCam), CHL1 (extravillous cytotrophoblast antigen) (Abnova), Cytokeratin 7 (AbCam), Cytokeratin 8 (AbCam), Cytokeratin 18 (AbCam), FAS-Associated Phosphatase-1 (Leica), Folate Binding Protein (AbCam), FD0161G, Glucose Transporter GLUT3, H315, H316, HAI-1 (Hepatocyte growth factor activator protein-1 (EBioscience)), Human Placental Lactogen (Serotec), Id-1, Id-2, IBSP (Integrin Binding SialoProtein), MCSF-Receptor, MNF116, OKT9, plasminogen activator inhibitor 1 (AbCam), PLP-A (prolactin like proteins A) (Millipore Corporation), PLP-B (prolactin like proteins B), PLP-C (prolactin like proteins C), PLP-D (prolactin like proteins D), PLP-F (prolactin like proteins F), PLP-L (prolactin like proteins L), PLP-M (prolactin like proteins M), PLP-N (prolactin like proteins N), SP-1 (trophoblast specific beta 1 glycoprotein) (AbCam, BD Pharmingen), SSEA (Stage Specific Embryonic Antigen) (Novus Biologicals), TA1, TA2, Tfeb, Troma1, Trop1 (EBioscience) and Trop2, URO-4 (Adenosine Deaminase Binding Protein [ABM]) (Covance). Fetal cells can also be isolated based on the expression of a combination of any two or more thereof. In some embodiments, the fetal cells are selected using an agent which binds syncytiotrophoblasts such as a monoclonal antibody which binds NDOG1. In other embodiments, the fetal cells are selected using combinations of agents which bind to villous syncytiotrophoblasts, villous cytotrophoblasts and extra villous cytotrophoblasts. For example, the combination of agents may include an agent which binds NDOG1 (Syncytiotrophoblasts), an agent which binds SP-1 (Villous Cytotrophoblasts and villous syncytiotrophoblasts), and an agent which binds HLA-G (ExtraVillous Cytotrophoblasts).

Once fetal cells are separated, they can be propagated in culture using methods known in the art. For example for propagating embryonic stem (ES) cells, ES cell medium can be used. This medium is 80% Dulbecco's modified Eagle's medium (DMEM; no pyruvate, high glucose formulation, GIBCO® BRL), with 20% fetal bovine serum (FBS; Hyclone), 0.1 mM β-mercaptoethanol (Sigma), 1% nonessential amino acid stock (GIBCO® BRL). Generally, primate ES cells are isolated on a confluent layer of murine embryonic fibroblast in the presence of ES cell medium. In one example, embryonic fibroblasts are obtained from 12 day old fetuses from outbred mice (such as CF1, available from SASCO), but other strains may be used as an alternative. Tissue culture dishes treated with 0.1% gelatin (type I; Sigma) can be utilized. Distinguishing features of ES cells, as compared to the committed "multipotential" stem cells present in adults, include the capacity of ES cells to maintain an undifferentiated state indefinitely in culture, and the potential that ES cells have to develop into every different cell types. Dissociated cells are re-plated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split manual disaggregation every 5-7 days as the cultures become dense. Early passage cells are also frozen and stored in liquid nitrogen. Cell lines can be karyotyped with a standard G-banding technique and compared to published karyotypes for the primate species.

Of course, a variety of cell culture methods are available in the art and can be used to propagate embryonic cells of interest. In some embodiments, the sample is seeded on the feeder layer for stem cell culture under sterile conditions. *Mycoplasma* and other contaminations can be examined. ESC-like cells can be examined by an Applied StemCell, Inc. ESC/iPSC characterization kit (immunofluorescence). Thus, the expression of OCT4, SOX2, SSEA4, TRA-1-60, and TRA 1-81 is examined.

Addition methods for isolating fetal cells from liquid samples are known and, in some embodiments, are used in the disclosed methods. For example, additional methods for isolating fetal cells include those disclosed in Patent Publications US20030013123, WO1990006509, WO1991007660, WO1995026417, WO1998002528, WO1998018005, WO2000071987, WO2003042405, WO2004076653, WO2005100401, WO2007106838, WO2007112281, and WO2009039507, each of which is incorporated by reference herein in its entirety.

IV. Detection of Chromosomal Abnormalities and Diagnostic Testing

In some embodiments, diagnostic testing is performed on cells and/or cellular components that are collected using the methods disclosed herein. The diagnostic test can detect, for example, the presence or absence of a cell type (e.g. see U.S. Pat. Nos. 5,124,252 and 5,965,375, each of which is incorporated by reference herein in its entirety), a protein (e.g. see U.S. Pat. Nos. 5,190,881 and 5,661,010, each of which is incorporated by reference herein in its entirety), a lipid, or a nucleic acid (e.g., see U.S. Pat. Nos. 5,538,851 and 5,459,034, each of which is incorporated by reference herein in its entirety).

In several embodiments, the diagnostic test is performed by a third party.

In several non-limiting examples, the cells or cellular components are analyzed to determine the response or absence of a genomic or epigenetic characteristic associated with a biological outcome (e.g., a phenotype exhibited by the subject from which the cells or cellular components are derived), such as the presence or absence of a Y chromosome, or the presence or absence of an aneuploidy (e.g. the presence or absence of more than two copies of chromosome 21).

In some specific, non-limiting examples, the cells or cellular components are analyzed to detect the presence of a Y chromosome, to determine if the fetus is male. In other embodiments the cells or cellular components are analyzed to detect chromosomal abnormalities in the fetus. These methods can include the separation of fetal cells, but in some embodiments fetal cells need not be separated from maternal cells.

The methods can include the isolation of cellular components such as DNA, RNA, proteins or lipids. The cellular component that is analyzed can be genetic material, including RNA, nuclear DNA or mitochondrial DNA. However, at least in some instances it may be informative to analyze RNA or protein. Furthermore, the DNA may encode a gene, or may encode a functional RNA which is not translated, or the DNA analyzed may even be an informative non-transcribed sequence or marker.

Methods for isolation of these components are known in the art. In some embodiments, the cellular components are collected directly from the sample. Cellular components can be extracted from the fetal cells present in the sample. Thus, in some embodiments, fetal cellular components, such as fetal DNA, RNA, protein and/or lipids are separated from the maternal cellular components, such as maternal DNA, RNA, proteins and/or lipids. However, for some analysis, the separation of fetal cellular components from maternal cellular components is not required. In some embodiments, a mixture of maternal and fetal cellular components are isolated from the absorbent medium, and these cellular components are then subjected to diagnostic testing for the fetus. In one specific, non-limiting example, the cellular components are tested for the presence of a Y chromosome, to determine if the fetus is male. In other embodiments the cellular components are analyzed to detect chromosomal abnormalities in the fetus.

DNA can be extracted and concentrated by known methods, including centrifugation and various enzyme inhibitors. In some embodiments, the DNA is bound to a selective membrane (e.g., silica) to separate it from contaminants. Fetal DNA can be hypomethylated relative to adult DNA reflecting transcriptional silencing of specific genes expressed early in development. One means of generating fetal-specific PCR products is to identify loci that are unmethylated in fetal DNA and methylated in adult/maternal DNA. Another means to detect fetal-specific DNA is to identify loci that are methylated in fetal DNA and unmethylated in adult/maternal DNA. Loci of this type are differentially reactive with bisulfite such that unmethylated Cs in DNA undergo oxidative deamination, resulting in C to U transitions. Methylated Cs are not reactive with bisulfite, and consequently, are unaffected. Bisulfite treatment of fetal and maternal DNA present in maternal serum will create primary sequence differences between fetal and maternal loci that exhibit differential methylation. However, restriction enzymes that differentially recognize and clear unmethylated DNA can also be used. In other embodiments, the method for selective enrichment of fetal DNA requires the use of the methyl-CpG binding domain of human MBD2 protein, which is coupled to paramagnetic beads, for example DYNABEADS®280 Streptavidin, via a biotin linker Without being bound by theory, the high affinity of the MBD-biotin protein for CpG-methylated DNA provides greater sensitivity than antibody binding, while the use of the DYNABEADS® provides a simplified, streamlined workflow.

In one embodiment, chromosomal abnormalities are detected. This includes a gross abnormality in a chromosome or the number of chromosomes. For example, this includes detecting trisomy in chromosome 21 which is indicative of Down's syndrome, trisomy 18, trisomy 13, sex chromosomal abnormalities such as Klinefelter syndrome (47, XXY), XYY or Turner's syndrome, chromosome translocations and deletions, a small proportion of Down's syndrome patients have translocation and chromosomal deletion syndromes which include Pradar-Willi syndrome and Angelman syndrome, both of which involve deletions of part of chromosome 15, and the detection of mutations (such as deletions, insertions, transitions, transversions and other mutations) in individual genes. Other types of chromosomal problems also exist such as Fragile X syndrome, hemophilia, spinal muscular dystrophy, myotonic dystrophy, Menkes disease and neurofibromatosis, which can be detected by DNA analysis.

Genetic abnormalities such as a single nucleotide substitution, deletion, insertion, micro-deletion, micro-insertion, short deletion, short insertion, multinucleotide substitution, and abnormal DNA methylation and loss of imprint (LOI) can be detected. Such a genetic abnormality can be related to an inherited genetic disease such as a single-gene disorder (e.g., cystic fibrosis, Canavan, Tay-Sachs disease, Gaucher disease, Familial Dysautonomia, Niemann-Pick disease, Fanconi anemia, Ataxia telengectasia, Bloom syndrome, Familial Mediterranean fever (FMF), X-linked spondyloepiphyseal dysplasia tarda, factor XI), an imprinting disorder [e.g., Angelman Syndrome, Prader-Willi Syndrome, Beckwith-Wiedemann syndrome, Myoclonus-dystonia syndrome (MDS)], or to predisposition to various diseases (e.g., mutations in the BRCA1 and BRCA2 genes). Other genetic disorders which can be detected by DNA analysis are known such as thalassaemia, Duchenne muscular dystrophy, connexin 26, congenital adrenal hypoplasia, X-linked hydrocephalus, ornithine transcarbamylase deficiency, Huntington's disease, mitochondrial disorder, mucopolysaccharidosis I or IV, Nome's disease, Rett syndrome, Smith-Lemli Optiz syndrome, 21-hydroxylase deficiency or holocarboxylase synthetase deficiency, diastrophic dysplasia, galactosialidosis, gangliosidosis, hereditary sensory neuropathy, hypogammaglobulinaemia, hypophosphatasia, Leigh's syndrome, aspartylglucosaminuria, metachromatic leukodystrophy Wilson's disease, steroid sulfatase deficiency, X-linked adrenoleukodystrophy, phosphorylase kinase deficiency (Type VI glycogen storage disease) and debranching enzyme deficiency (Type III glycogen storage disease). These and other genetic diseases are mentioned in The Metabolic and Molecular Basis of Inherited Disease, 8th Edition, Volumes I, II, III and IV, Scriver, C. R. et al. (eds), McGraw Hill, 2001. Clearly, any genetic disease where the gene has been cloned and mutations detected can be analyzed.

The methods can also be used to determine the sex of the fetus. For example, staining of the isolated fetal nuclei with a Y chromosome specific marker will indicate that the fetus is male, whereas the lack of staining will indicate that the fetus is female.

In yet other embodiments, the methods described herein can be used for paternity testing. Where the paternity of a child is disputed, the procedures of the invention enable this issue to be resolved early on during pregnancy by testing fetal cells. Many procedures have been described for parentage testing which rely on the analysis of suitable polymorphic markers. Polymorphic markers include any nucleic acid change (e.g., substitution, deletion, insertion, inversion), variable number of tandem repeats (VNTR), short tandem repeats (STR), minisatellite variant repeats (MVR) and the like. Typically, parentage testing involves DNA fingerprinting targeting informative repeat regions, or the analysis of highly polymorphic regions of the genome such as HLA loci.

Chromosomal abnormalities, either in structure or number, can be detected by karyotyping. Karyotyping analysis is generally performed on nuclei which have been arrested during mitosis by the addition of a mitotic spindle inhibitor such as colchicine. In some embodiments, a Giemsa-stained chromosome spread is prepared, allowing analysis of chromosome number as well as detection of chromosomal translocations.

The genetic assays can involve any suitable method for identifying mutations or polymorphisms in the fetal DNA, such as: sequencing of the DNA at one or more of the relevant positions; differential hybridization of an oligonucleotide probe designed to hybridize at the relevant positions of either the wild-type or mutant sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for the wild-type sequence and unmatched for the mutant sequence or vice versa; or the selective introduction of a restriction site using a PCR (or similar) primer matched for the wild-type or mutant genotype, followed by a restriction digest. The assay may be indirect, such that it is capable of detecting a mutation at another position or gene which is known to be linked to one or more of the mutant positions. The probes and primers can be fragments of DNA isolated from nature or may be synthetic. A non-denaturing gel can be used to detect differing lengths of fragments resulting from digestion with an appropriate restriction enzyme. The DNA is usually amplified before digestion, for example using the polymerase chain reaction (PCR) method and modifications thereof.

Amplification of fetal DNA can be achieved by the established PCR methods or by developments thereof or alternatives such as quantitative PCR, quantitative fluorescent PCR (QF-PCR), multiplex ligation dependent probe amplification, digital PCR, real time PCR (RT-PCR), single nuclei PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

Generally, an "appropriate restriction enzyme" will recognize and cut the wild-type sequence and not the mutated sequence or vice versa. The sequence which is recognized and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognizes a sequence which occurs only rarely. In another method, a pair of PCR primers are used which hybridize to either the wild-type genotype or the mutant genotype but not both. Whether amplified DNA is produced will then indicate the wild-type or mutant genotype (and hence phenotype).

Another method employs similar PCR primers but, as well as hybridizing to only one of the wild-type or mutant sequences, they introduce a restriction site which is not otherwise there in either the wild-type or mutant sequences. In order to facilitate subsequent cloning of amplified sequences, primers may have restriction enzyme sites appended to their 5' ends. Thus, all nucleotides of the primers are derived from the gene sequence of interest or sequences adjacent to that gene except the few nucleotides necessary to form a restriction enzyme site. Such enzymes and sites are well known in the art. The primers themselves can be synthesized using techniques which are well known in the art. Generally, the primers can be made using synthesizing machines which are commercially available.

PCR techniques that utilize fluorescent dyes may also be used to detect genetic defects in DNA from fetal cells isolated by the methods disclosed herein. Fluorescent dyes can be used to detect specific PCR amplified double stranded DNA product (e.g. ethidium bromide, or SYBR Green I). The 5' nuclease (TTAQMAN®) assay can be used which utilizes a specially constructed primer whose fluorescence is quenched until it is released by the nuclease activity of the Taq DNA polymerase during extension of the PCR product. Assays based on Molecular Beacon technology can be used which rely on a specially constructed oligonucleotide that when self-hybridized quenches fluorescence (fluorescent dye and quencher molecule are adjacent). Upon hybridization to a specific amplified PCR product, fluorescence is increased due to separation of the quencher from the fluorescent molecule. Assays based on Amplifluor (Intergen) technology can be used which utilize specially prepared primers, where again fluorescence is quenched due to self-hybridization. In this case, fluorescence is released during PCR amplification by extension through the primer sequence, which results in the separation of fluorescent and quencher molecules. Assays that rely on an increase in fluorescence resonance energy transfer can be used which utilize two specially designed adjacent primers, which have different fluorochromes on their ends. When these primers anneal to a specific PCR amplified product, the two fluorochromes are brought together. The excitation of one fluorochrome results in an increase in fluorescence of the other fluorochrome.

The acronym "FISH" references a technique that uses chromophore tags (fluorophores) that emit a secondary signal if illuminated with an excitation light to detect a chromosomal structure. FISH uses fluorescent probes which bind only to those parts of the chromosome with which they show a high degree of sequence similarity. Such tags may be directed to specific chromosomes and specific chromosome regions. The probe has to be long enough to hybridize specifically to its target (and not to similar sequences in the genome), but not too large to impede the hybridization process, and it should be tagged directly with fluorophores. This can be done in various ways, for example nick translation or PCR using tagged nucleotides. If signal amplification is necessary to exceed the detection threshold of the microscope (which depends on many factors such as probe labeling efficiency, the kind of probe and the fluorescent dye), secondary fluorescent tagged antibodies or streptavidin are bound to the tag molecules, thus amplifying the signal.

Any known sequencing methods can be used to analyze DNA. Such sequencing methods provide sequence information at the single nucleotide level and thus allow for the detection of mutations and other abnormalities that occur in one genotype in the biological sample, but not the other.

EXAMPLES

The following examples are provided to illustrate particular features of certain embodiments, but the scope of the claims should not be limited to those features exemplified.

Example 1

Collection of Fetal DNA

For this study, interlabial pads (PADKIT®) were used for collection of samples containing the products of approximately 2-6 hours of cervicovaginal discharge (maternal vaginal sample). Each PADKIT® contains two (2) interlabial pads (one for the sample, and one extra), a plastic glove, a collection vial containing a preservative solution, inside a transport tube, and a special self-addressed envelope.

Figure 1B:
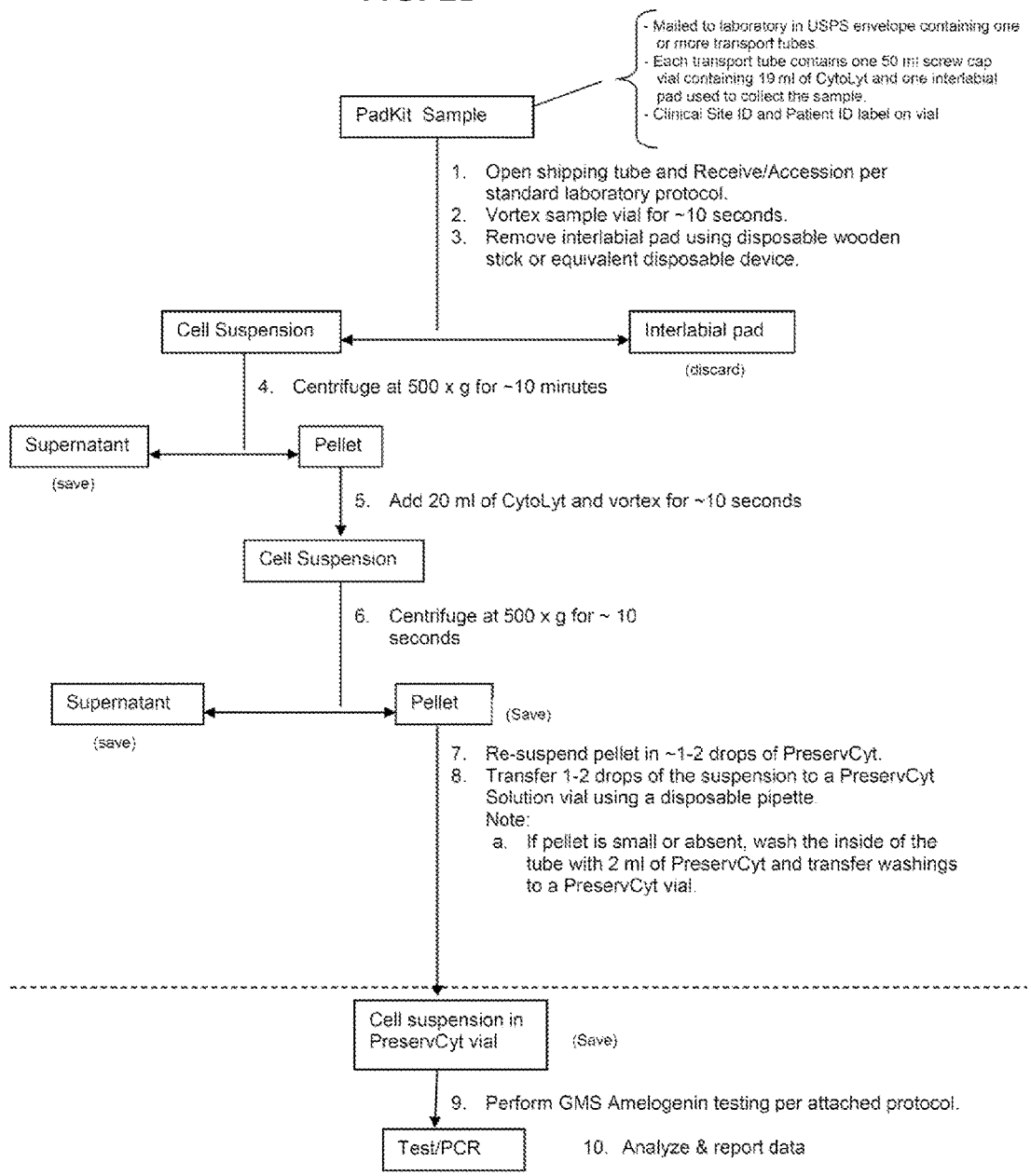

The goals were to determine if fetal DNA was present in a maternal vaginal sample, and comparing the performance of a new specimen collection method with the ultrasound outcome in a targeted population of women, known to be pregnant with a male child. The design of this study involved home-based sample collection, and included a blinded analysis of results developed from study samples. This study was designed to compare maternal vaginal samples collected with the PADKIT® to other methods of fetal sex determination by the identification of the "Y" chromosome within the maternal sample. The Y chromosome of the child is identical to the Y chromosome of the father. Thus, the participants were asked to abstain from all sexual intercourse during the period from 24 hours prior to ultrasound screening, until the sample collection was completed, so that Y chromosomes from sperm will not contribute to DNA measurements for fetal cells. The study design is shown in FIG. 1.

Following enrollment, the study subject began the self-collection of maternal vaginal samples using the supplies provided in the PADKIT®. Each subject collected two vaginal PADKIT® samples over two days, beginning 1 day, but not more than 14 days after ultrasound sex determination. Each PADKIT® interlabial pad was kept in place 2-4 hours, one sample taken each day, after first morning void.

Maternal Vaginal Sample Collection:
1. Two (2) maternal vaginal samples were collected.
2. Subject collected one maternal vaginal sample each morning for two days, beginning 1 day, but not more than 14 days, after ultrasound testing.
3. A Specimen Collection Log entry was completed for each sample by the study subject, and forwarded to the Study Coordinator.
4. A Vial Label, traceable to the Specimen Collection Log entry, was completed and affixed to the collection vial for each sample collected.
5. Specimens were forwarded to a US based laboratory, via US mail.
6. At the completion of the Study, the residual fraction of all samples were sent to, and stored at QuantRx for future development work Sample Handling/Processing/Analysis
1. The PADKIT® sample, in a vial, was forwarded to a US-based laboratory for testing.
2. The Lab received the sample, assigned a unique accessioning/tracking number and recorded the information specified on the Specimen Receipt Log.
3. The Sample Processing/Interpretation Performed Included:
    a) Elution of the cellular material from the interlabial pad
    b) Removal of the interlabial pad from the vial.
    c) Centrifugation of the vial.
    d) Using the cell pellet for preparation of genomic tests
    e) Evaluation of the tests.
4. A description of findings was completed for each specimen.

Example 2

Clinical Study

Figure 2:
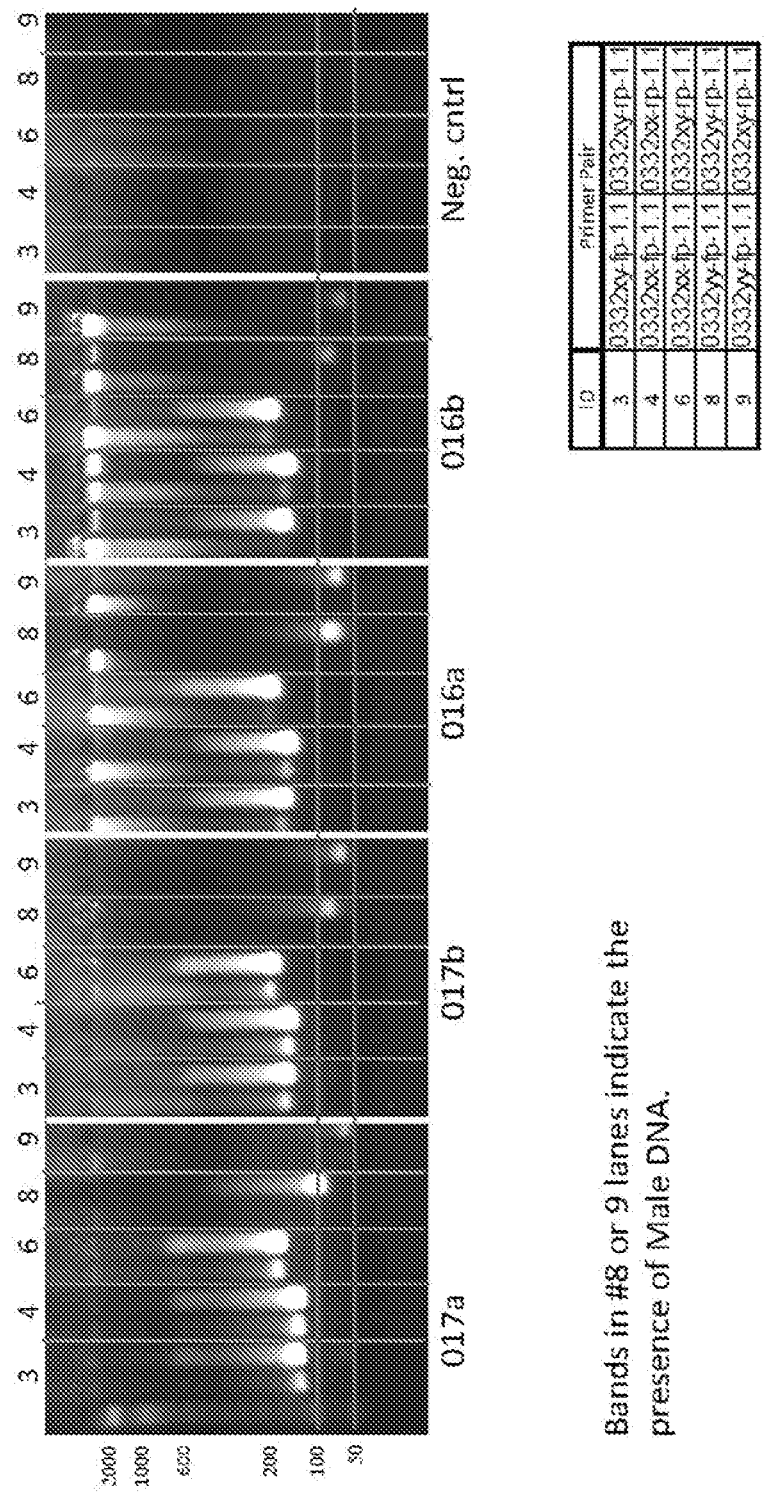
FIG. 2 is an analysis of genetic material showing the presence of male DNA in samples collected from pregnant females known to be carrying boys. A single-center study was performed, focused on OB/GYN Centers with access to pregnant patients with an identified male fetus. The design of this study involved home-based sample collection, and included blinded testing from study samples. Diagnosis was compared to ultrasound outcome. Subjects were screened based on ultrasound results. Women enrolled in the study were required to collect two (2) vaginal samples, within 14 days of the ultrasound results. There were no abnormal clinical follow-ups after completion of this study.
Figure 3:
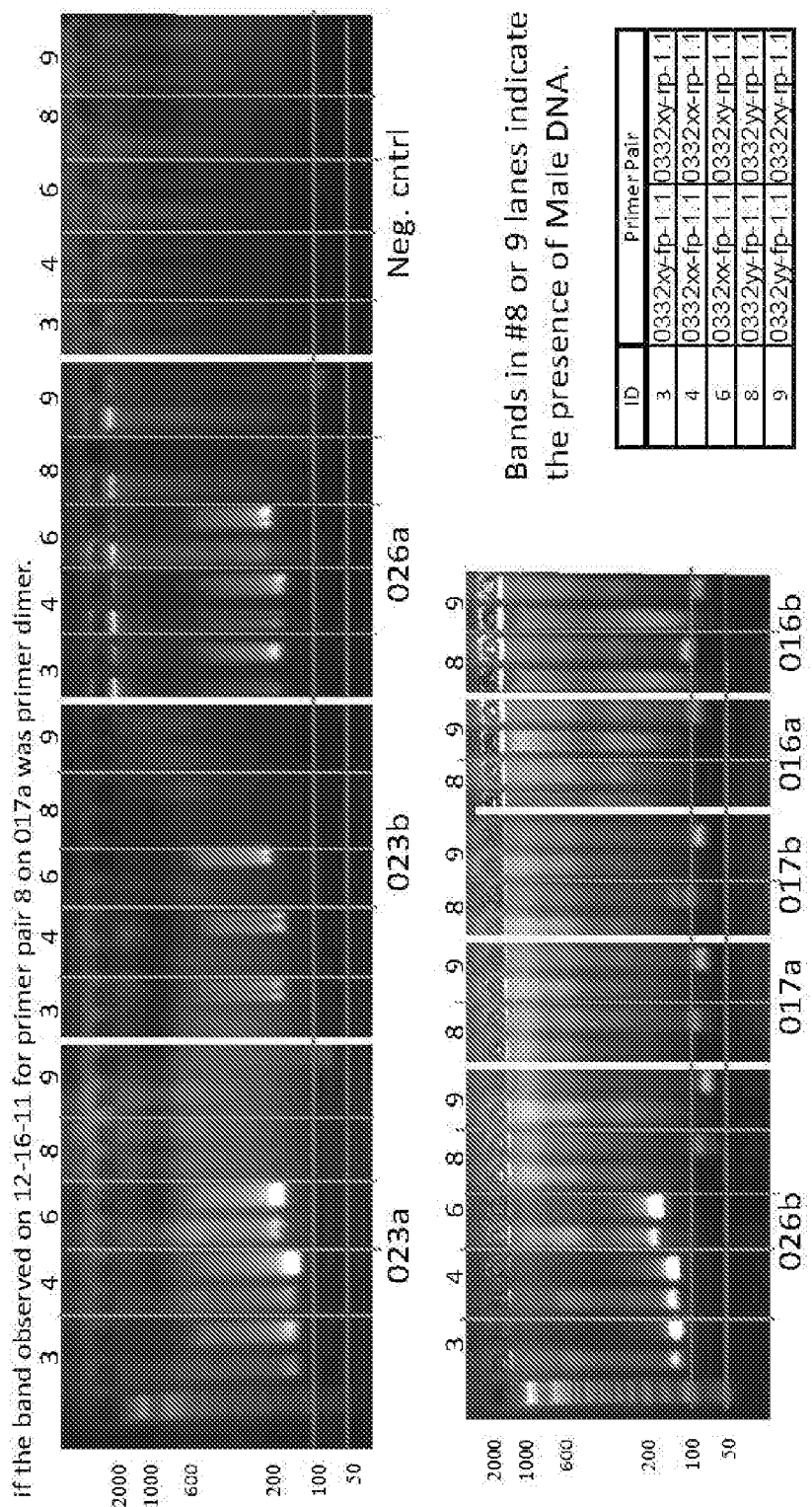
FIG. 3 is an additional analysis of genetic material showing the presence of male DNA in samples collected from pregnant females known to be carrying boys.

Study Objectives:
    PADKIT® samples obtained from patients post ultrasound identification of fetal sex (male)
Study Design:
    Home-based sample collection was used to perform blinded testing from study samples.
Study Sample:
    Pregnant women, who have opted to identify the sex of their fetus via ultrasound, were enrolled.
    Ultrasound identification of a male fetus
    Collect and mailed two (2) PADKIT® samples, and abstain from intercourse from 24 hours prior to the Ultrasound screening until the collection process is complete.
Results:
    Ten (10) samples+two (2) controls have been tested
    100% of the samples are positive for the "Y" chromosome
    Controls are clearly negative for "Y" chromosome
    All Study Samples are positive for "Y" chromosome
    All Study Samples have been shipped 6,873 miles FIGS. 2 and 3 show the study results wherein fetal ("Y") DNA was detected in the samples.

FIGS. 4 and 5 show the cytology results.

Sample Collection:The subjects were provided with two (2) PADKIT® packets for collecting maternal vaginal samples. Each PADKIT® contained the following:

Two (2) interlabial pads. One for your sample, Two extras if needed

One (1) disposable glove

Subjects placed the first interlabial pad, and began collecting the first sample within 24 hours of returning home from the clinic. They were instructed not to start the study if they had sexual intercourse since entering into the study protocol. They placed the second interlabial pad and began collecting that sample within 12 hours after retrieving the first sample and placed it in the transport vial. They were instructed that they were providing two maternal vaginal samples; this process will take between 2 to 6 hours for each sample, and 4 hours was considered optimal. There were also instructed to empty their bladder completely; and not to urinate until after the sample was taken.

Instructions for inserting and removing the interlabial pad were:

Stand or sit comfortably, with knees spread apart—allowing the labial (vaginal) lips to open.

Hold the interlabial pad with the thumb and finger, and gently press it between the vaginal lips.

When the knees are brought together and stand up, the vaginal lips naturally folded around the interlabial pad, holding it in place.

The interlabial pad was retained in place for 2 to 6 hours; with 4 hours considered optimal.

When the pad was removed, the opened sample vial was placed on a counter, the used pad was placed in the vial, the lid was closed and placed in a mailer for shipping to the test facility.

PADKIT® Sample QC Via Digital PAP Cytometry in a CLIA/CAP Certified Laboratory: Upon harvest as a pellet, ½ of each PADKIT® sample was subjected to digital cytometry using standard HOLOGICS® Thin-prep technology and Pap staining performed at a CLIA-certified Cytometry lab. These Thin-prep slides were then analyzed by APERIO® digital cytometry. Representative data are shown in FIG. 5. Both standard light and digital cytometry confirmed that all samples processed for this study showed ordinary cell morphology, which as assessed by the Cytometry lab, were indistinguishable relative to routine PAP stained cervical scrapes. See FIGS. 4-5.

In order to obtain the ability to detect signal from the male version of the Amelogenin (Amel-Y) marker gene in the presence of a 100 to 10,000 fold excess of the very similar female version of Amelogenin on the X chromosomes of the mother (Amel-X), Y-specific tandem PCR reactions were run, followed by hybridization to the Y-Chip. Positive hybridization signals for the six Y-specific hybridization probes (y1-y6) were seen for all samples except for non-pregnant control samples 22A,B and 25A,B. The data demonstrate good false positive signal behavior (no X-specific signals for any sample) and no Y-specific signals on the X0X (female) controls 22A,b & 25A,B. (FIGS. 2-3)

1 uL of the retained PadKit cell suspension in Tris not used for Cytometry (typically 50 uL) was subjected to same sort of tandem PCR reactions described above for Amelogenin, but previously optimized for HLA-Typing at GMS. In these pilot HLA-Typing studies, the raw cell pellets from 12 anonymous participants were obtained via PADKIT® collection. They were subjected to HLA-Typing at the DRB1 locus. The 2° PCR amplicon product derived from the DRB1 amplification reactions was analyzed on an agarose gel, to generate the expected 250 bp DRB1 2° amplicon product (FIG. 6). This Cy-3 labeled amplicon was then used as the target for standard HLA-Chip analysis in the 576 probe (12 well) format.

It was determined that the cells were viable for 48 hours in shipment. Cells remain viable for up to 5 years when refrigerated.

Example 3

Collection of Fetal Cells Using an Interlabial Pad

This example describes a method for collecting and isolating fetal cells from a pregnant female using an interlabial pad. An interlabial pad (e.g., as included with the PADKIT® available from QuantRx, Corp., and described herein is used to collect a biological sample from the pregnant subject, for example, as described in Examples 1 and 2 above. The biological sample is collected from the pad by centrifugation to form a pellet, which includes cells from the biological sample, as well as other material. Cell pellets obtained from the interlabial pad contain both maternal cells and various types of fetal cells. For example, the fetal cells are shed from the placenta into the vaginal fluid and are captured by the interlabial pad. The fetal cells (including pluripotent human embryo stem cells) are separated from the maternal cells to facilitate study and use of the fetal cells, including analysis of the genome of the fetus. Once obtained, the pellet is stored at 4° C. until further processing.

A confirmation step can optionally be performed, to confirm that fetal cells are present in the cell pellet obtained from the interlabial pad. Fetal cells can be detected by determining if protein markers for fetal cells, such as alpha-fetoprotein (AFP), H-19 protein, yes associated protein (YAP65), and osteopontin, are present in a sample of the pellet obtained from the interlabial pad. Alternatively, fetal cells can be detected by determining if embryonic stem cells are present in a present in a sample of the pellet obtained from the interlabial pad, for example by determining if markers for embryonic stem cells (such as ssEA4, TRA-1-60, and TRA-1-81 proteins) are present on cells in the sample of the pellet obtained from the interlabial pad, for example by processing the sample with an embryonic stem cell (ESC)/induced pluripotent stem cell (iPSC) characterization kit (e.g., as available from Applied StemCell, Inc., Cat. No. ASK-3006) for human ESCs according to the manufacturer's directions. Antibodies for use to purify fetal cells from the pellet obtained from the interlabial can be selected based on the degree and intensity of staining of fetal cells in the confirmation step.

Fetal cells in the pellet obtained from the interlabial pad are isolated, e.g., from maternal cells in the pellet. Fetal cells can be positively, and/or maternal cells can be negatively, selected using a variety of techniques well known in the art, including cell sorting, for example by fluorescence activated cells sorting (FACS) and/or affinity purification (such as using an affinity reagent bound to a solid phase particle which can be isolated on the basis of the properties of the solid phase particles for example beads (e.g., colored latex beads or magnetic particles). For example, the fetal cells can be separated from maternal cells based on positive selection by FACS or affinity purification using a fetal marker, such as expression of alpha-fetoprotein (AFP), H-19 protein, yes associated protein (YAP65), or osteopontin protein. Further, fetal stem cells (such as ESCs) can be separated from maternal cells based on positive selection by FACS or affinity purification using a fetal ESC marker, such as expression of ssEA4, TRA-1-60, or TRA-1-81 protein The pellet obtained from the interlabial pad is washed (e.g., three times) with appropriate buffer, such as PBS. The washed cells are incubated with an antibody specific for a fetal cell specific protein marker (such as AFP). The antibody is directly labeled with a fluorescent marker (such as fluoroscein) or with a magnetic bead. The labeled cells are washed three times to remove non-specifically bound antibody.

In some examples, incubation of the antibody with the cells obtained from the interlabial pad causes the cells to clump together. In this event, the clumped cells (including mostly cells bound by the antibody, that is, fetal cells) can be separated from non-clumped cells (including mostly cells not bound by the antibody, that is, maternal cells) by low-speed centrifugation. This additional purification step is typically performed prior to separation of cells based on FACS or affinity purification. The labeled (fetal) cells are sorted from non-labeled (maternal) cells using FACS (if the antibody is labeled with a fluorescent marker) or magnetic separation (if the antibody is labeled with a magnetic bead). The sorting step can be repeated multiple times (such as three times) to increase purity of the isolated fetal cells. The sorted fetal cells can be processed for further analysis (such as determination of the fetal genotype), and/or expanded in tissue culture for future use.

It will be apparent that the precise details of the methods or compositions described may be varied or modified without departing from the spirit of the described embodiments. We claim all such modifications and variations that fall within the scope and spirit of the claims below.

It is claimed:

1. A method of obtaining fetal stem cells, comprising
   placing an absorbent medium in an interlabial space external to a vaginal opening of a pregnant female with an intact amniotic sac,
   collecting vaginal fluid comprising cells in the absorbent medium while the absorbent medium is in the interlabial space;
   removing the absorbent medium;
   extracting the vaginal fluid from the absorbent medium;
   isolating fetal stem cells from the vaginal fluid extracted from the absorbent medium, wherein isolating the fetal stem cells comprises separating the fetal cells from maternal cells in the vaginal fluid using an antibody that specifically binds to TRA-1-60, thereby obtaining the fetal stem cells.

2. The method of claim 1, wherein the absorbent medium is at least partially, or substantially entirely, placed in the interlabial space for about 2 to about 6 hours.

3. The method of claim 1, wherein the absorbent medium comprises rayon, cellulose, cotton, other natural fibers, or synthetic materials.

4. The method of claim 1, wherein the absorbent medium is in the form of an interlabial pad.

5. The method of claim 4, wherein the interlabial pad includes a major portion and a minor portion, and wherein the absorbent medium is removed by gripping the minor portion and removing the interlabial pad.

6. The method of claim 1, wherein isolating the fetal stem cells from the absorbent medium comprises:
   releasing cells from the absorbent medium with a physiological buffer;
   collecting the physiological buffer;
   centrifuging the physiological buffer to form a pellet of cellular material; and
   suspending the cellular material in a physiological buffer.

7. The method of claim 6, wherein releasing cells from the absorbent medium comprises the use of vibration or soniciation.

8. The method of claim 1, further comprising analyzing the genome and/or epigenome of at least one fetal cell at a locus of interest.

9. The method of claim 8, wherein analyzing the genome comprises determining the presence or absence of a Y chromosome.

10. The method of claim 1, wherein analyzing the genome comprises the use of polymerase chain reaction.

11. The method of claim 10, wherein analyzing the epigenome comprises determining a degree of methylation or histone modification of an epigenomic locus.

12. The method of claim 1, further comprising culturing at least one of the fetal stem cells in a tissue culture medium.

13. The method of claim 12, further comprising propagating the fetal stem cell in vitro.

14. The method of claim 13, further comprising differentiating the fetal stem cell in vitro.

* * * * *